(12) United States Patent
Wei et al.

(10) Patent No.: US 10,823,608 B2
(45) Date of Patent: Nov. 3, 2020

(54) DEVICE AND SYSTEM FOR PERSONAL UV EXPOSURE MEASUREMENTS

(71) Applicant: L'OREAL, Paris (FR)

(72) Inventors: Pinghung Wei, San Francisco, CA (US); Rafal Pielak, Richmond, CA (US); Yunzhou Shi, San Bruno, CA (US); Edouard Messager, Saint-Ouen (FR); Guive Balooch, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/236,803

(22) Filed: Dec. 31, 2018

(65) Prior Publication Data

US 2019/0204146 A1   Jul. 4, 2019

Related U.S. Application Data

(60) Provisional application No. 62/611,884, filed on Dec. 29, 2017.

(51) Int. Cl.
*G01J 1/42* (2006.01)
*G01J 1/02* (2006.01)
(Continued)

(52) U.S. Cl.
CPC ............ *G01J 1/429* (2013.01); *A61B 5/7275* (2013.01); *G01J 1/0209* (2013.01);
(Continued)

(58) Field of Classification Search
CPC .. G01J 1/429; G01J 2001/4266; G01J 1/0219; G01J 1/44; G01J 1/0271; G01J 1/0233; G01J 1/0403; G01J 1/4204; G01J 2001/444; G01J 1/0204; G01J 2001/0257; G01J 1/0228; G01J 1/0238; G01J 1/0437; G01J 1/0492; G01J 1/4209; G01J 1/0266; G01J 1/42; G01J 2003/1213; G01J 3/0264; G01J 3/0272; G01J 3/0283; G01J 3/0291; G01J 3/10; G01J 3/42; G01J 3/4406;
(Continued)

(56) References Cited

U.S. PATENT DOCUMENTS

| 4,188,799 | A | * | 2/1980 | Saccoccio | ............... | A44C 7/008 |
| | | | | | | 411/436 |
| 9,024,271 | B2 | * | 5/2015 | Aslam | ................... | G01J 1/0233 |
| | | | | | | 250/372 |

(Continued)

FOREIGN PATENT DOCUMENTS

WO    WO 2016/196673 A1   12/2016

OTHER PUBLICATIONS

International Search Report and Written Opinion dated May. 7, 2019 in PCT/US2018/068124, 13 pages.

*Primary Examiner* — Michael P Stafira
(74) *Attorney, Agent, or Firm* — Oblon, McClelland, Maier & Neustadt, L.L.P.

(57) ABSTRACT

A system is provided for determining personal ultra-violet (UV) radiation measurements. The system may include a measurement device configured to measure UV irradiation; and a terminal device configured to receive an output of the measured UV irradiation from the measurement device and to display a specific user's personal UV exposure risk level based on at least the measured sun irradiation.

14 Claims, 49 Drawing Sheets

(51) Int. Cl.
*A61B 5/00* (2006.01)
*G01J 1/44* (2006.01)

(52) U.S. Cl.
CPC ........... *G01J 1/0219* (2013.01); *G01J 1/0271* (2013.01); *G01J 1/44* (2013.01); *A61B 2560/0242* (2013.01); *G01J 2001/0257* (2013.01); *G01J 2001/4266* (2013.01)

(58) Field of Classification Search
CPC ...... G01J 1/0209; G01J 1/0295; G01J 1/4228; G01J 5/10; A61B 2560/0242; A61B 5/441; A61B 2562/0219; A61B 5/0205; A61B 5/02433; A61B 5/0537; A61B 5/1112; A61B 5/1118; A61B 5/14552; A61B 5/0024; A61B 5/01; A61B 5/021; A61B 5/02416; A61B 5/1126; A61B 5/14551; A61B 5/6824; A61B 5/721; A61B 5/681; A61B 2560/0475; A61B 5/0004; A61B 5/0059; A61B 5/445; A61B 5/4809; A61B 5/74; A61B 5/742; A61B 5/746; A61B 2560/0209; A61B 2560/0252; A61B 2562/0223; A61B 3/107; A61B 5/0002; A61B 5/0022; A61B 5/02427; A61B 5/02438; A61B 5/0402; A61B 5/0488; A61B 5/0533; A61B 5/067; A61B 5/112; A61B 5/1121; A61B 5/1123; A61B 5/14517; A61B 5/4812; A61B 5/489; A61B 5/6831; A61B 5/684; A61B 5/7203; A61B 5/7214; A61B 5/7221; A61B 18/1815; A61B 18/20; A61B 18/24; A61B 2018/00577; A61B 2018/00642; A61B 2018/00672; A61B 2018/00904; A61B 2018/00982; A61B 2560/0214; A61B 2562/0271; A61B 2562/028; A61B 3/10; A61B 3/101; A61B 3/135; A61B 3/145; A61B 5/0066; A61B 5/0071; A61B 5/0095; A61B 5/412; A61B 5/415; A61B 5/416; A61B 5/418; A61B 5/4857; A61B 5/6826; A61B 5/6898; A61B 5/7275; A61B 8/06; A61B 8/08; A61B 8/085; A61B 8/4281; A61B 8/4477; A61B 8/481
See application file for complete search history.

(56) References Cited

U.S. PATENT DOCUMENTS

| | | | |
|---|---|---|---|
| 2008/0134720 A1* | 6/2008 | Harder | A44C 7/005 63/14.1 |
| 2012/0253152 A1* | 10/2012 | Haisley | A61B 5/1455 600/323 |
| 2013/0186136 A1* | 7/2013 | Crafton | A44C 7/002 63/14.1 |
| 2014/0358012 A1 | 12/2014 | Richards et al. | |
| 2016/0305819 A1* | 10/2016 | Lian | G01J 1/44 |
| 2017/0069192 A1* | 3/2017 | Sood | G01J 1/429 |
| 2017/0191866 A1* | 7/2017 | Balooch | G01J 1/429 |
| 2018/0274973 A1* | 9/2018 | Rogers | G06K 19/0716 |

\* cited by examiner

| Part Number | Description | Manufacturer | Components Number | Quantity | Note |
|---|---|---|---|---|---|
| RF430FRL152H8GRFID Transponders Sensor Transponder | | Texas Instruments | U1 | 1 | NFC chip for communication and data processing |
| SML206UV-385-IL | EMITTER UV 398NM 25MA 1206 | Bivar Inc. | U2 | 1 | UVA LED for converting UV radiance to electrical current |
| CPH325A | CAP 11MF 3.3V SURFACE MOUNT | Seiko Instruments | C1 | 1 | Super Capacitor for storing electrical charges generated by UV LED |
| CSD17383F4 | MOSFET N-CH 30V 3.1A 0402 | Texas Instruments | M1 | 1 | MOSFET, acting as a controllable switch to reset the super cap. |
| ERJ-1GEF1001C | RES SMD 1K OHM 1% 1/20W 0201 | Panasonic Electronic Components | R1 | 1 | 1k resistor, passive components for improving the discharging rate |
| C1005X5R0J225KO 50BC | CAP CER 2.2UF 6.3V X5R 0402 | TDK Corporation | C2 | 1 | capacitor, passive component for NFC |
| C0603X7R1A102KO 30RA | CAP CER 1000PF 10V X7R 0201 | TDK Corporation | C3 | 1 | capacitor, passive component for NFC |
| C0603X5R1A104KO 30BC | CAP CER 0.1UF 10V X5R 0201 | TDK Corporation | C4, C5 | 2 | capacitor, passive component for NFC |

Fig. 2D

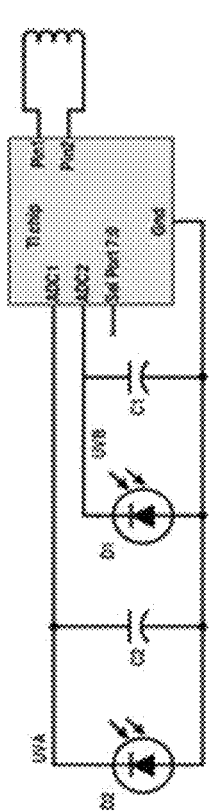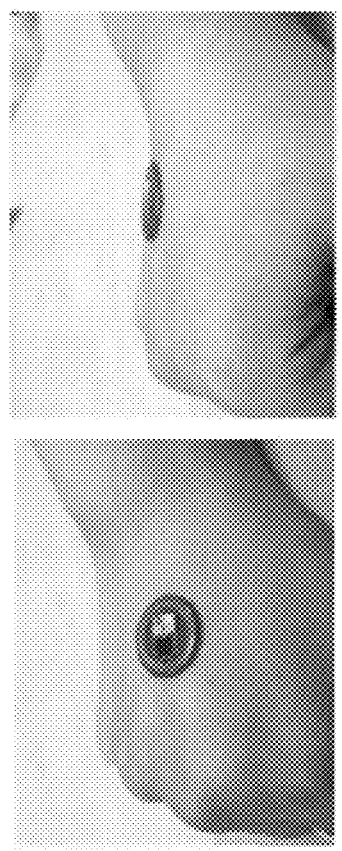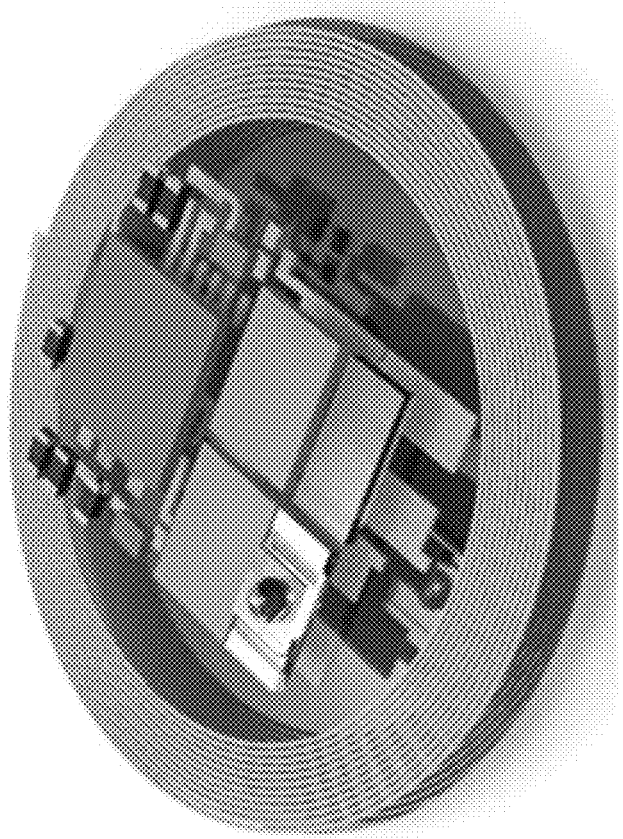
Fig. 4

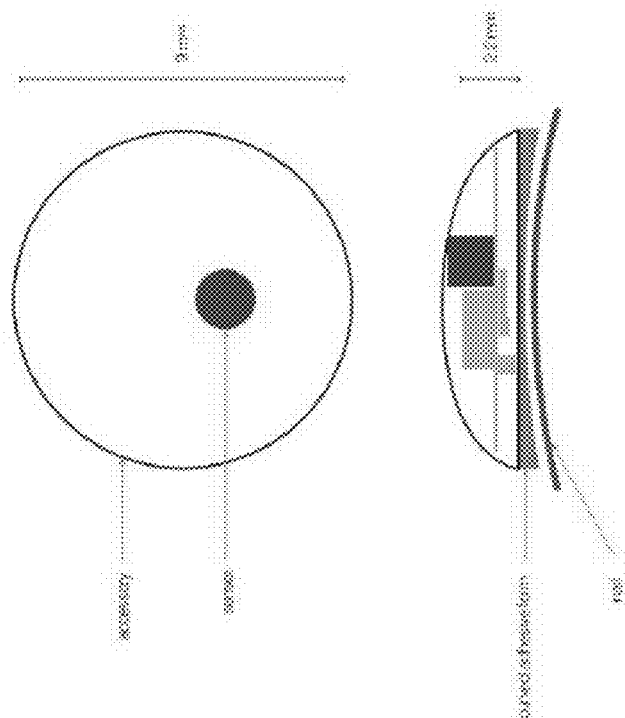
Fig. 7B

bracelet
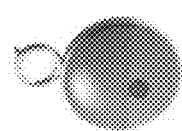
charm
clip D
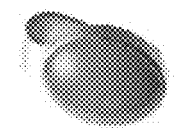
clip C
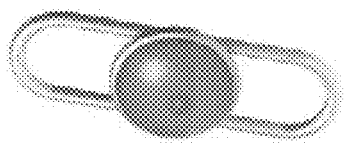
clip B
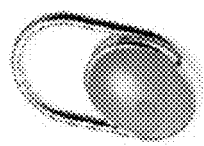
clip A
Fig. 8B

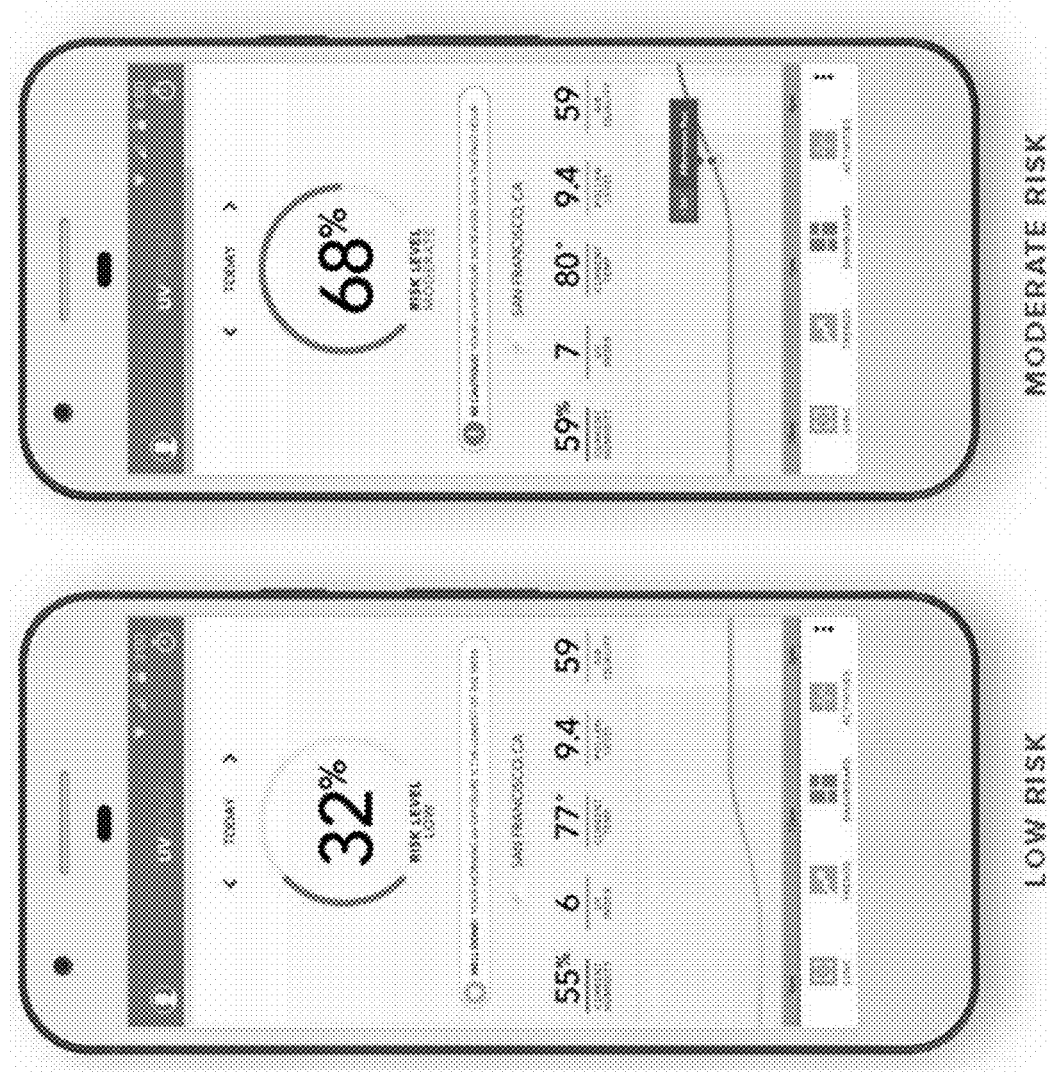

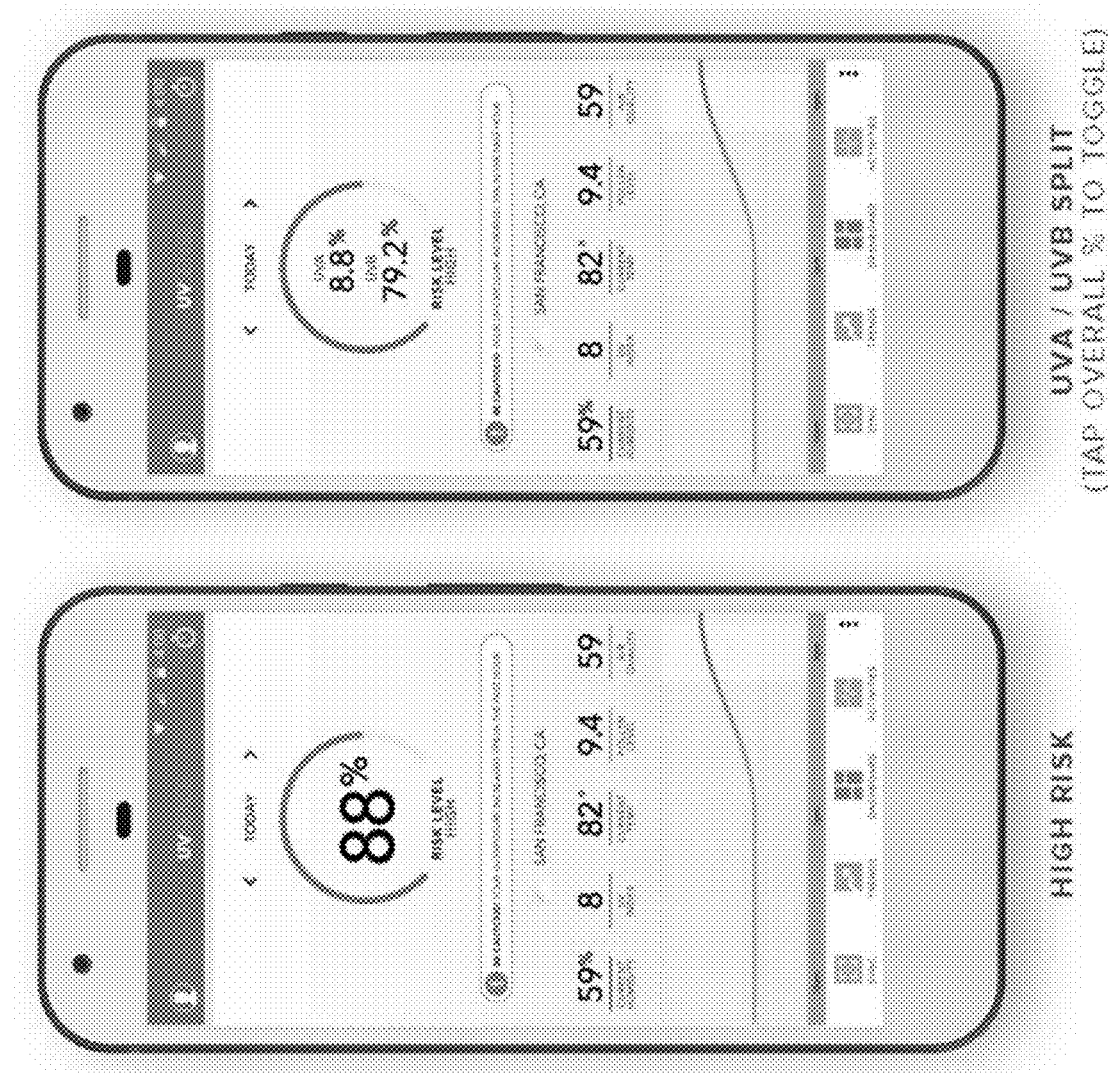
Fig. 9C HIGH RISK
Fig. 9D UVA / UVB SPLIT (TAP OVERALL % TO TOGGLE)

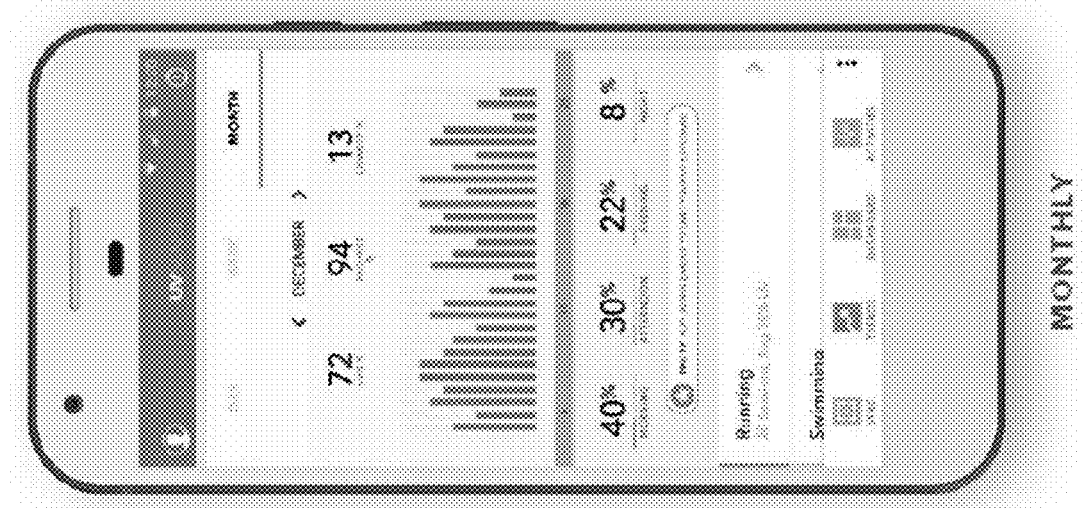
Fig. 9G MONTHLY
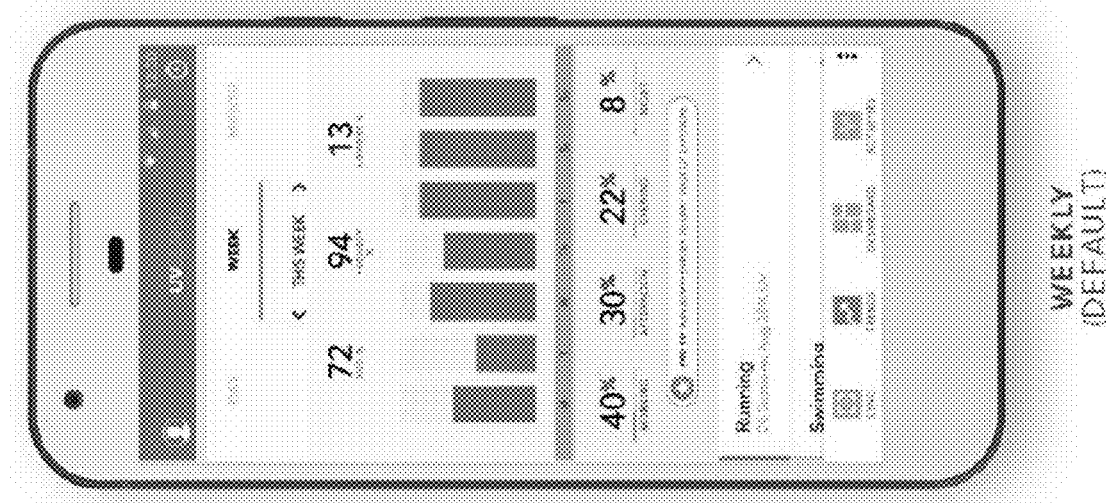
Fig. 9F WEEKLY (DEFAULT)
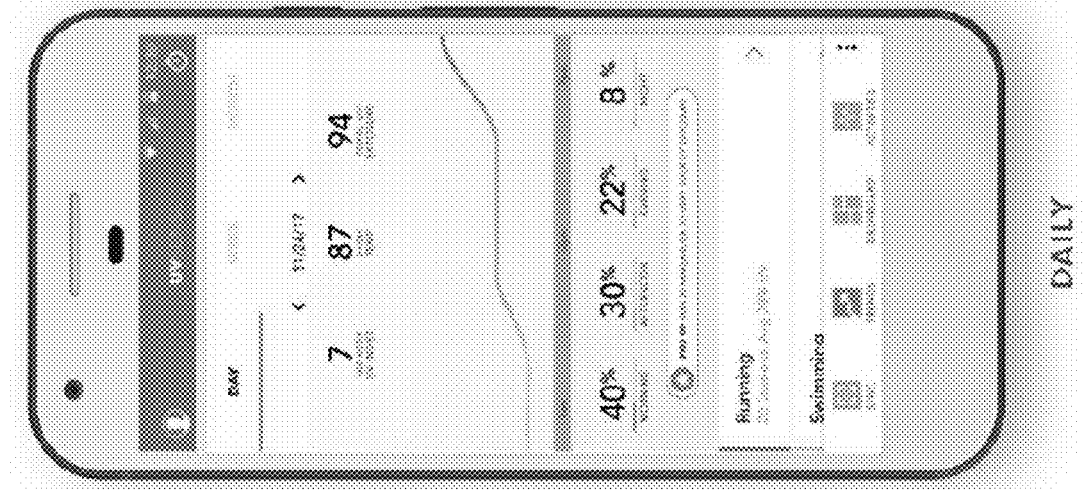
Fig. 9E DAILY

Fig. 9I PROFILE
Fig. 9H SYNC

Fig. 9K ACTIVITY DETAIL
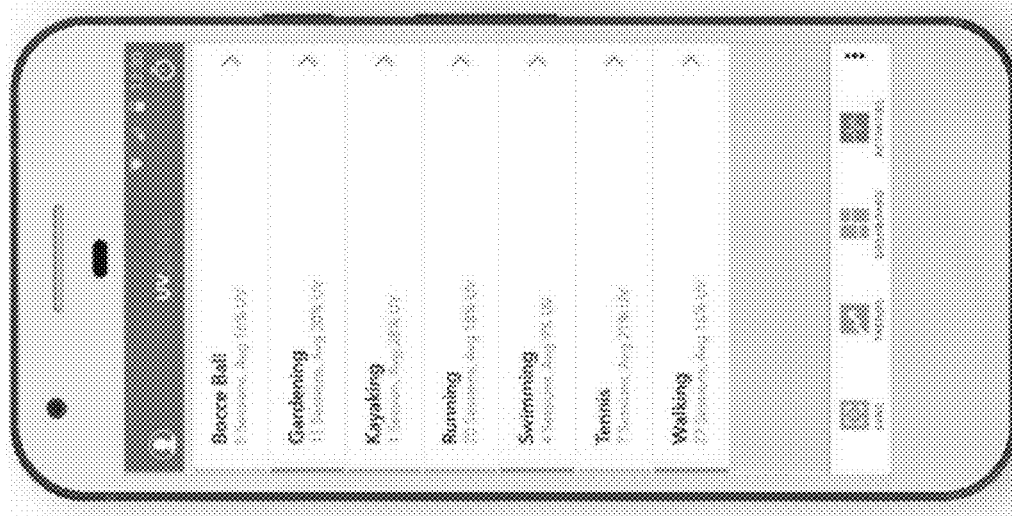
Fig. 9J ACTIVITIES

| Morning Session | | | | | |
|---|---|---|---|---|---|
| | SC | RBH | LBH | LOA | LIA |
| SC<br>Scienterra UVA | 1.00000 | 0.54026<br><.0001 | 0.65600<br><.0001 | 0.79280<br><.0001 | 0.20042<br>0.1543 |
| Noon Session | | | | | |
| | SC | RBH | LBH | LOA | LIA |
| SC<br>Scienterra UVA | 1.00000 | 0.54026<br><.0001 | 0.65600<br><.0001 | 0.79280<br><.0001 | 0.20042<br>0.1543 |
| Afternoon Session | | | | | |
| | SC | RBH | LBH | LOA | LIA |
| SC<br>Scienterra UVA | 1.00000 | 0.76201<br><.0001 | 0.78217<br><.0001 | 0.66562<br><.0001 | 0.46611<br>0.0014 |

Pearson Correlation Coefficients, N = 52, Results showed significant correlation between the Scienterra dosimeter vs. Right Back Hand, Left Back Hand, and Left Outer Arm Sensors during Day 1 sessions.

Fig. 18B

Day 2 results, comparing electronic UV sensors vs. Scienterra dosimeter at Beach and City during normal activities (no water)

DEVICE AND SYSTEM FOR PERSONAL UV EXPOSURE MEASUREMENTS

CROSS-REFERENCE TO RELATED APPLICATIONS

This application claims the benefit of priority from U.S. Application No. 62/611,884 filed Dec. 29, 2017, the entire contents of which are incorporated herein by reference.

BACKGROUND

Field

The present disclosure relates to a system and method for determining an amount of UV exposure for a particular user based on a detection of the UV exposure at a location of the user and specific information regarding the particular user.

Description of Related Art

Excessive ultraviolet (UV) radiation has acute and chronic effects on the skin, eye and immune system. Personalized monitoring of UV radiation is thus paramount to measure the extent of personal sun exposure, which could vary with environment, lifestyle, and sunscreen use.

UV radiation is essential for production of vitamin D and beneficial for human health, but over-exposure to UV has many associated risk factors, including skin cancer and photo-aging, even long after UV exposure ends. The acute effects of excessive UVA and UVB exposure are usually short-lived and reversible. Such effects include erythema, pigment darkening and sunburn. Prolonged exposures even to sub-erythemal UV doses result in epidermal thickening and degradation of keratinocytes, elastin, collagen and blood vessels, thus leading to premature skin aging. Clinical symptoms usually include increased wrinkling and loss of elasticity. Studies have also shown that both UVA and UVB radiation have local and systemic immunosuppressive properties, which is believed to be an important contributor to skin cancer development. UV-induced DNA damage is an important factor in developing all types of skin cancer including melanoma, non-melanoma skin cancers, basal cell carcinoma and squamous cell carcinoma. Both UVA and UVB are strongly scattered by air, aerosols, and clouds. For high sun angles, when most of the UV arrives, cloud effects are similar at UVA and UVB wavelengths; however, for low sun conditions, the UVB attenuation tends to be stronger. Unlike UVB, UVA penetrates glass windows and therefore may result in excessive UV exposures even in an indoor environment. In addition, UVA readily passes through the ozone layer resulting in higher intensities of the UVA portion of the solar spectrum at the earth surface. Continuous sunscreen protection and monitoring of personal UV exposures is therefore critical for better skin protection and prevention of skin cancer.

However, conventional wearable devices are rigid, bulky, and not compatible with sunscreens.

Additionally, a previous device for detecting UV exposure has been described in U.S. PG Publication No. 2017/0191866A1, which is incorporated herein by reference.

SUMMARY

In an embodiment, a device is provided that is configured to measure ultra-violet (UV) radiation exposure, comprising: an electronic element configured to detect UV radiation exposure, circuitry configured to transmit detected UV radiation exposure to an external device.

In an embodiment, the electronic element is a UV sensitive LED.

In an embodiment, the circuitry includes a near field communication device.

In an embodiment, the device further includes a flexible material which encapsulates the electronic element and the circuitry.

In an embodiment, the device is configured to attach to a user's fingernail.

In an embodiment, the device is configured to attach to a wearable accessory.

In an embodiment, the wearable accessory is one of a ring, wristband, clip, charm, and bracelet.

In an embodiment, the circuitry is configured to transmit the detected UV radiation exposure to the external device at regular intervals.

In an embodiment, the circuitry is configured to transmit the detected UV radiation exposure to the external device at upon request from the external device.

In an embodiment, a system is provided for determining personal ultra-violet (UV) radiation measurements, comprising: a measurement device configured to measure UV irradiation; and a terminal device configured to receive an output of the measured UV irradiation from the measurement device and to display a specific user's personal UV exposure risk level based on at least the measured sun irradiation.

In an embodiment, the terminal device is configured to receive the measured UV irradiation from the measurement device at regular intervals over a predetermined time period, and display the specific user's personal UV exposure risk level based the measured sun irradiation taken over the entire predetermined time period.

In an embodiment, the terminal device is configured to correlate information related to specific user activities over the predetermined time period to the measured sun irradiation received from the measurement device.

In an embodiment, the terminal device is configured to correlate information of a skin type of the user and the measured UV irradiation received from the measurement device.

In an embodiment, the terminal device is configured to output a recommended method of protection or action based on the measured UV irradiation received from the measurement device.

In an embodiment, a method is provided, implemented by a system for determining personal ultra-violet (UV) radiation measurements, comprising: measuring, with a measurement device, UV irradiation; and receiving, by a terminal device, an output of the measured UV irradiation from the measurement device and displaying a specific user's personal UV exposure risk level based on at least the measured sun irradiation.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein:

FIGS. 2A-2F show examples of the sensor design and structure according to an embodiment.

FIG. 4 shows a three-dimensional view of the device layout of the sensor and a schematic diagram for the sensor.

FIGS. 7A-7B an alternative version of the UV sensor that is configured to be attached to a surface of user's fingernail according to an embodiment.

FIGS. 8B-8D shows alternative versions of the UV sensor as a clip, charm, bracelet, or attachment to sunglasses or a wristwatch according to embodiments.

FIGS. 9A-9K show examples of displays shown on an application that is executed on a client device according to embodiments.

DETAILED DESCRIPTION

Figure 1:
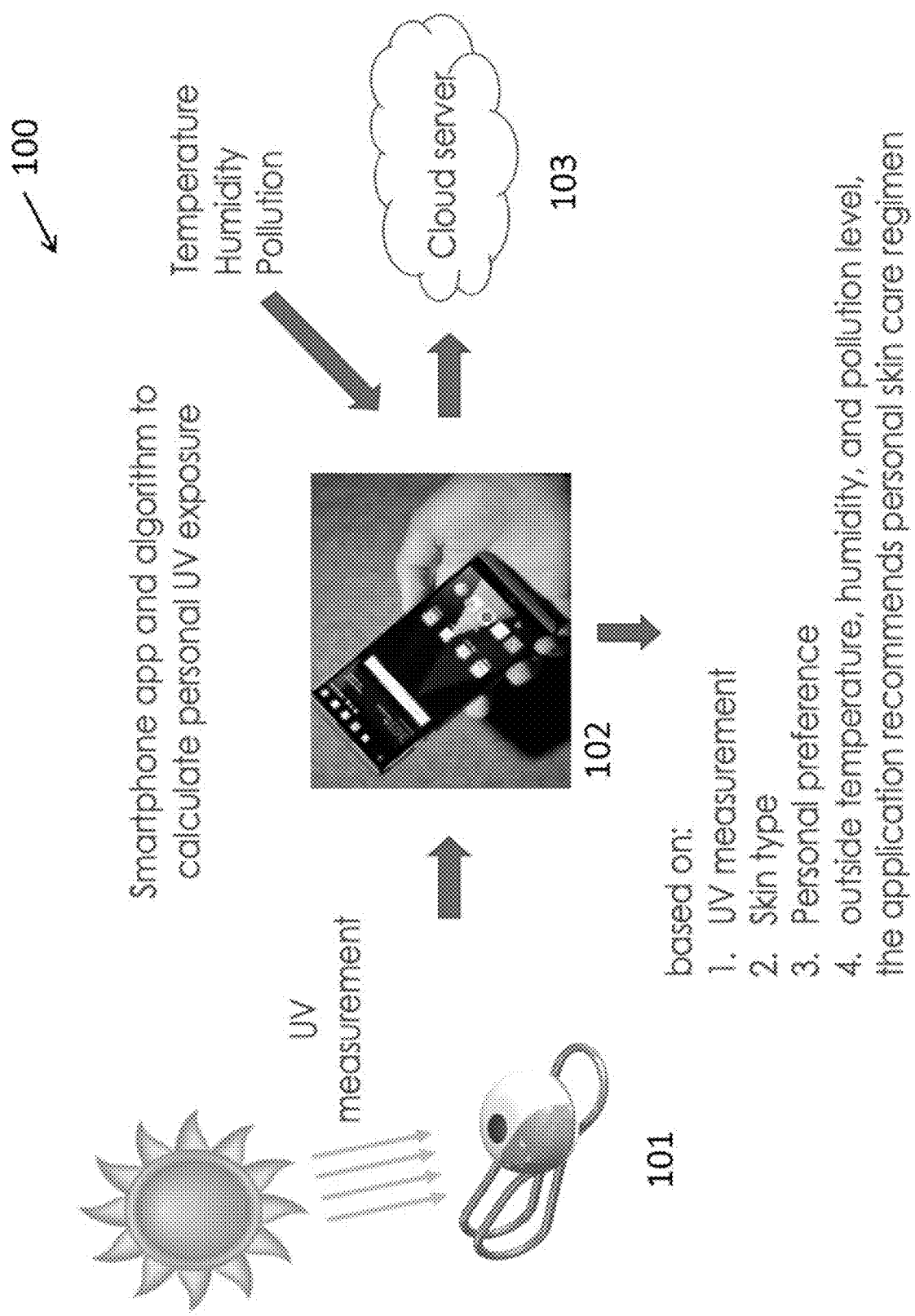
FIG. 1 shows a system for personal UV exposure measurements according to an embodiment.

FIG. 1 illustrates a system 100 for personal UV exposure measurements. It can be seen that the system includes one or more measurement sensor devices 101 (a Wearable Electronic UV sensor). Each of the devices 101 may connect to a client device 102, which may be a computer, tablet, personal digital assistant, or smartphone. The device 101 may be referred to as a "sensor" or "UV sensor" throughout this description and it is configured to be attached to a body part of the user. The client device is configured to receive an input from the user on the user's skin type in order to determine personal UV level.

The client device 102 is further configured to connect to a cloud computing environment 103 which is connected to data analytics servers for determining personalized UV doses for the user based on information provided by the client device according to the above-noted inputs.

It can be seen that outputs provided from an application on the client device 102 may be based on UV measurement, skin type, personal preference, and the environment (outside temperature, humidity, and pollution level). The application may further recommend a personal skin care regimen based on the measurements. The smartphone (client device) can include circuitry and hardware as is known in the art. The smartphone may include a CPU, an I/O interface, and a network controller such as BCM43342 Wi-Fi, Frequency Modulation, and Bluetooth combo chip from Broadcom, for interfacing with a network. The hardware can be designed for reduced size. For example, the CPU may be an APL0778 from Apple Inc., or may be other processor types that would be recognized by one of ordinary skill in the art.

Alternatively, the CPU may be implemented on an FPGA, ASIC, PLD or using discrete logic circuits, as one of ordinary skill in the art would recognize. Further, the CPU may be implemented as multiple processors cooperatively working in parallel (such as a cloud computing environment) to perform the instructions of the inventive processes described above.

The UV sensor is a battery-less, flexible, and ultra-small wearable skin sensor designed to measure UV exposure accurately via electronic sensors. The UV sensor can be connected to a smartphone application to collect the accumulative UV exposure over time, with adjustable sensitivity and resettable memory.

The sensor contains UV sensitive LED that will induce electronic current proportional to UV exposure. The amount of UV exposure then can be converted and stored as voltage, which is a measurement of accumulative UV exposure over time. The sensor is designed with NFC RFID and antenna, for user to obtain the data wirelessly via a smartphone application.

The integrated RFID/Microcontroller allows information to be stored on the device, such as personal data, skin phototype, location, and user IDs. The smartphone application is designed for customers to track their daily life UV dosage, with predictive algorithm to monitor Vitamin D level, UV aging, and sun safety.

The sensor can be worn on the skin or attached to various accessories with adhesive since the ultra-small footprint (<1.5 cm in diameter). The sensor is designed for up to 7 days wearability on the skin.

The system allows achievement the following objectives:
1. Daily Life UV Monitoring: Daily UV dosage, sunscreen reminder, forecast
2. Health Tracking: Personal UV trends and Vitamin D tracking
3. Personalized Applications: Comprehensive questionnaire and customized reminders
4. Predictive Information: Predict skin appearance ages based on user's UV exposure behaviors
5. Clinical application: in-vivo and in-vitro sunscreen evaluation. UV dose determination:

The sensor contains a UV sensitive LED that will induce electronic current proportional to UV exposure. The voltage is read each time as the user scans the sensor and the app converts the voltage to UVA dosage based on the calibrated correlations.

The corresponding UVB exposure is calculated using a pre-computed lookup table that gives the conversion factor as function of the column amount of ozone in the atmosphere and solar zenith angle (SZA). SZA is determined based on GPS location and time. The user latitude, longitude, and time are also used to extract the forecast ozone amount from satellite-measurements.

The UVA and UVB doses calculated by the app represents the amount of UV exposure that user was exposed to during a period between two consecutive scans. The user can follow their UV exposure over time and determine their personal daily safe UV dose and risk level.

Personal Daily Safe UV Doses and Risk Levels

The personal daily safe UV doses are calculated based on the skin phototype and minimal erythema dose (MED) The skin phototype is determined by a questionnaire completed by the user when the user first opens the app. The maximal daily safe UV dose is set to 0.8 MED. The rate of change of the UV exposure throughout the day is calculated for every scan for the time between the current and previous patch scan. In additional, daily, weekly, monthly, and yearly UV dose can be calculated.

Connectivity

The device is connected to the cloud server. The data is uploading to the server whenever a data network is available. The data can be analyzed on the device and on the server while the results are available for users via the smartphone application. Users can access their data on the cloud server to examine their UV exposure patterns over time at different locations.

Figure 2A:
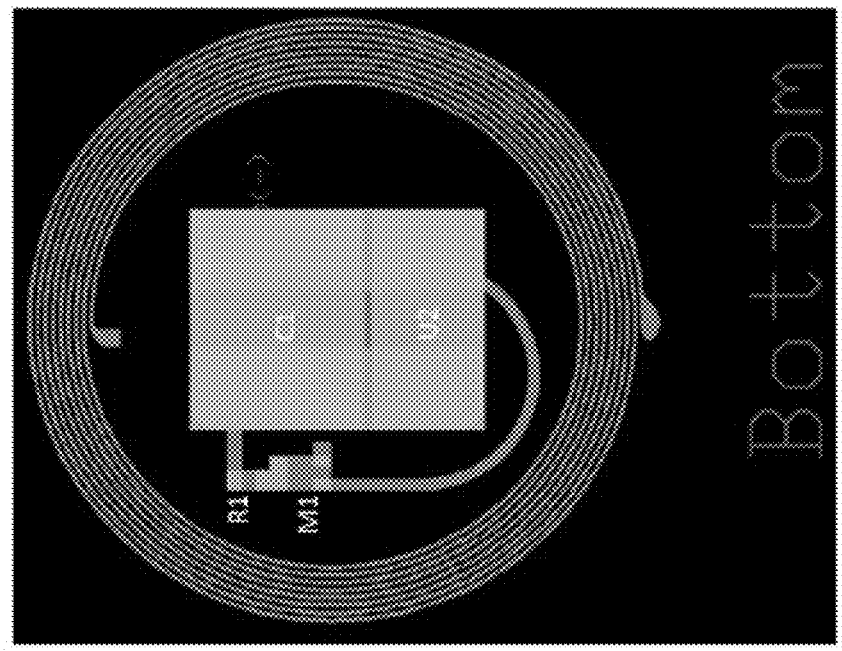
Figure 2B:
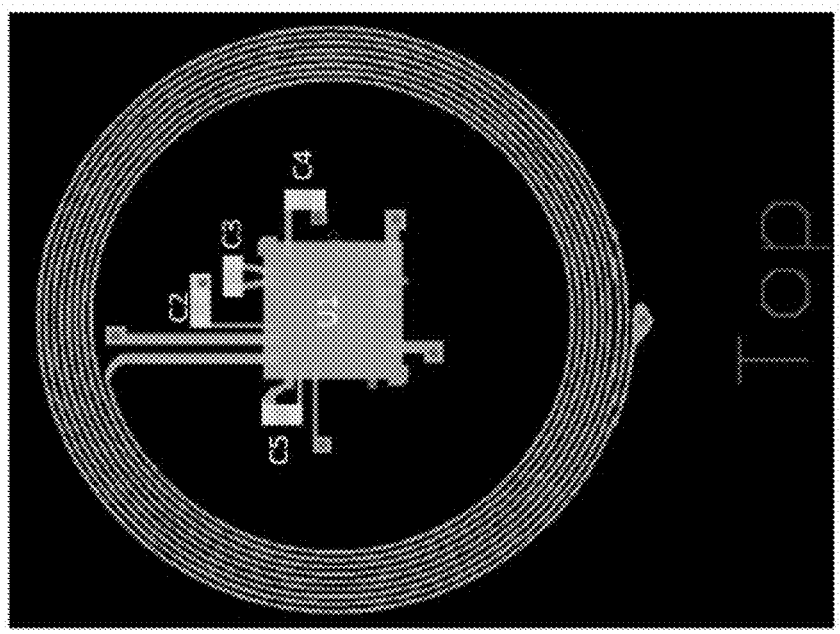
Figure 2C:
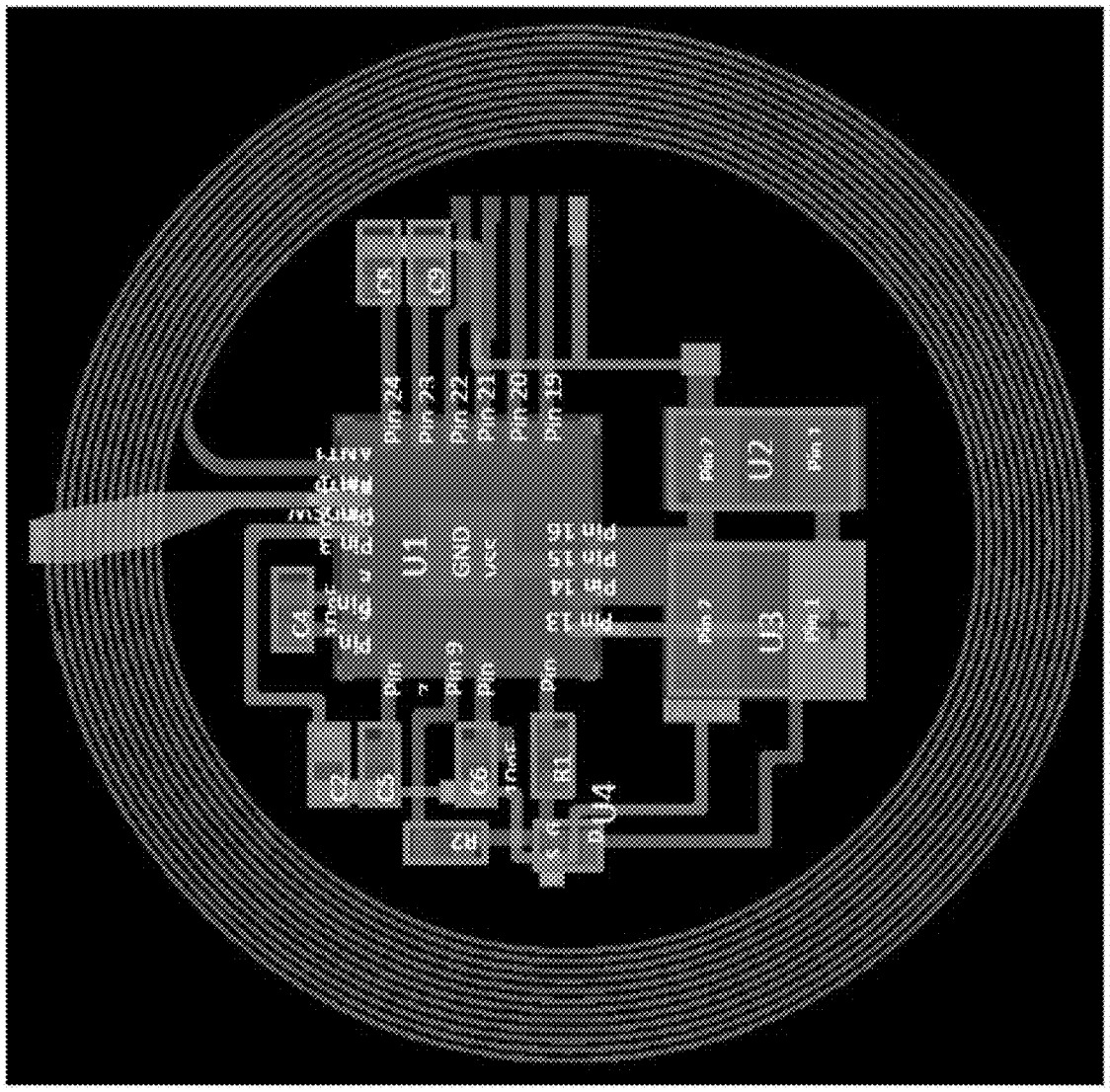

The device is encapsulated with Ecoflex 30, so it is waterproof for daily usage. FIGS. 2A-2C show examples of the sensor design and structure. The device includes:
- a two layer near field communication device with a Texas Instruments NFC packaged chip
- loop antenna (Cu, ~18 μm thick, diameter: 16 mm, width: 75 μm)
- polyimide film (PI, 18 μm thick) UVA diode as a photo-detector
- Super capacitor
- Device encapsulated with a clear polydimethylsiloxane ~50 u thick medical grade skin-adhesive.

The figure above shows the layout of the sensor. The layout is designed for standard flexible printed-circuit-board process. Notable components are:

TABLE 1.1

Components Descriptions

| Components ID | Part Name | Description |
| --- | --- | --- |
| U1 | RF430 | NFC chip for communication, data measurement, and resetting the memory |
| U2 | UVA LED | Surface mounted LED for generating electronic current under UV Exposure (UVA) |
| U3 | Super Cap | Capacitor as a memory to store the electronic charges generated by UV Exposure |
| U4 | P-MOSFET Transistor | A controllable switch for resetting the capacitor |

A more specific listing of the components is shown in FIG. 2D.

Figure 2E:
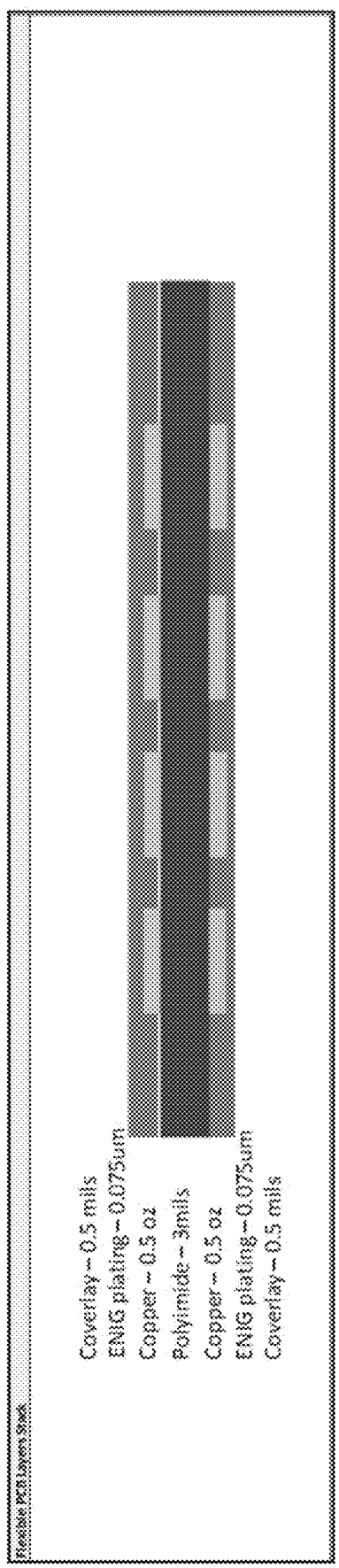

Details regarding flexible PCB layers stack is shown in FIG. 2E.

Figure 2F:
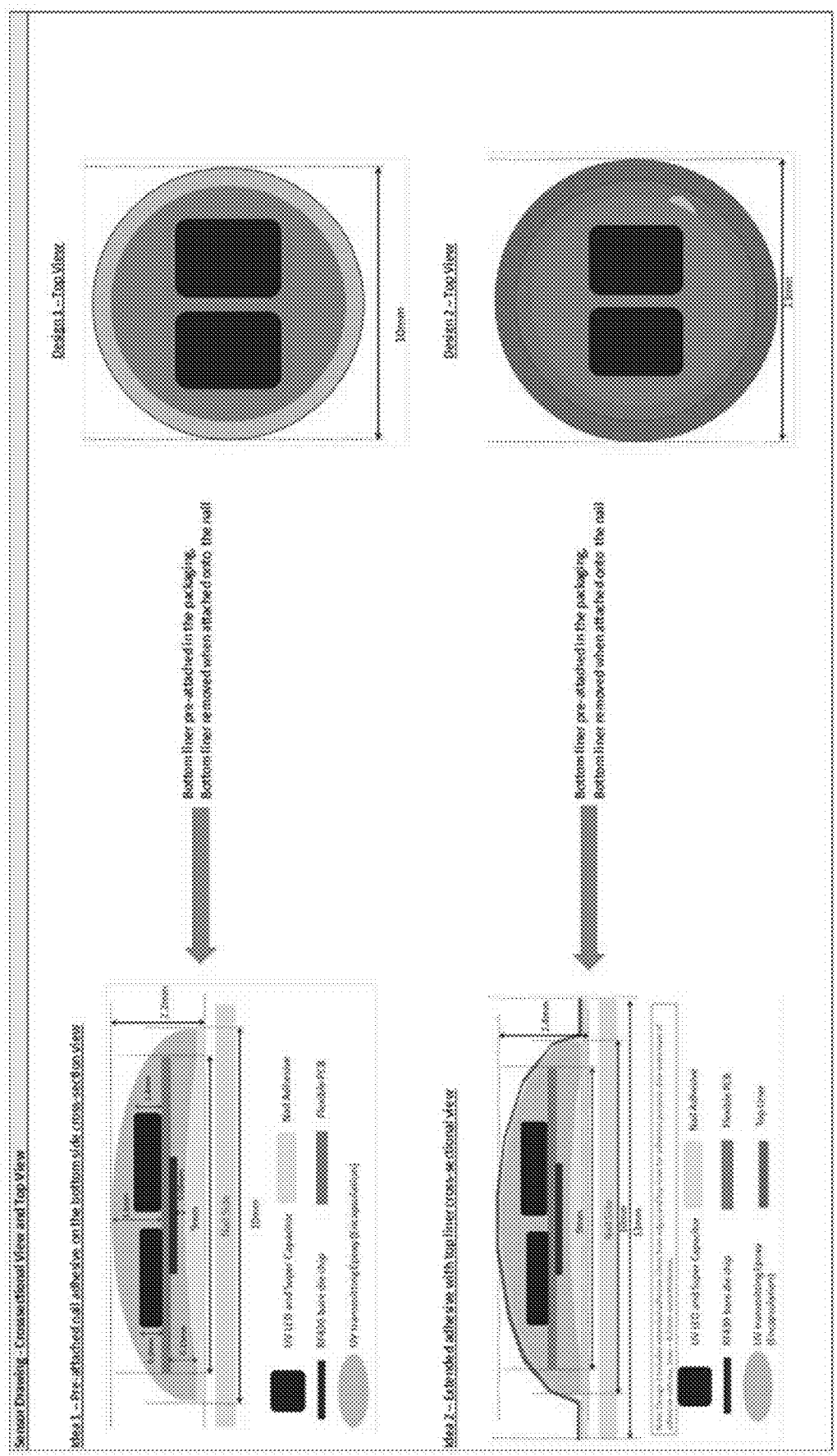

Different architecture designs of the sensor are shown in FIG. 2F.

The UVA LED is connected in parallel with the Super Cap, thus whenever the LED is under UV Exposure, electronic current will be generated and charged up the Super Cap. The amount of electronic charges is stored in the Super Cap can be measured by the RF430 Analog-To-Digital (ADC0) channel. The gate of P-MOSFET Transistor is controlled by the I/O channel of RF430 chip. When the transistor is turned on, Super Cap will be discharged and reset thus the sensor can be used again.

The Antenna is designed with standard flexible Printed-circuit-board design rules for manufacture-able process, and matched the standard NFC communication protocol with resonant frequency at 13.56 MHz. When the sensor is connected with a smartphone by NFC, the application can read the data and reset the capacitors for following measurements.

Figure 3:
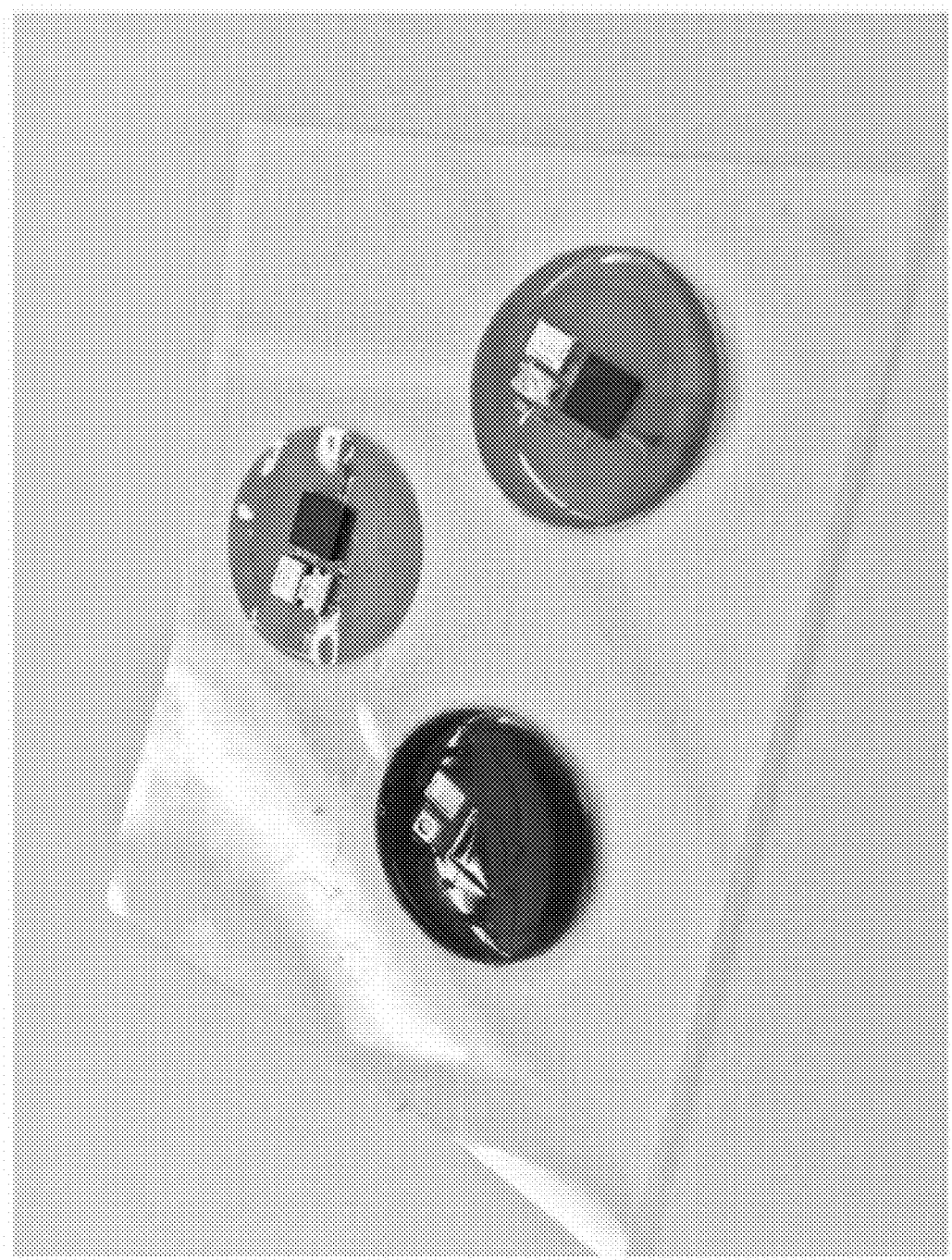
FIG. 3 shows different types of the sensors encapsulated and non-encapsulated according to an embodiment.

FIG. 3 shows different types of the sensors encapsulated and non-encapsulated with Ecoflex 30. FIG. 3 shows a bare sensor with no encapsulation, an encapsulated sensor with blue dye, and a transparent encapsulated sensor.

FIG. 4 shows a 3D view of the device layout of the sensor and a schematic diagram for the sensor.

Figure 5A:
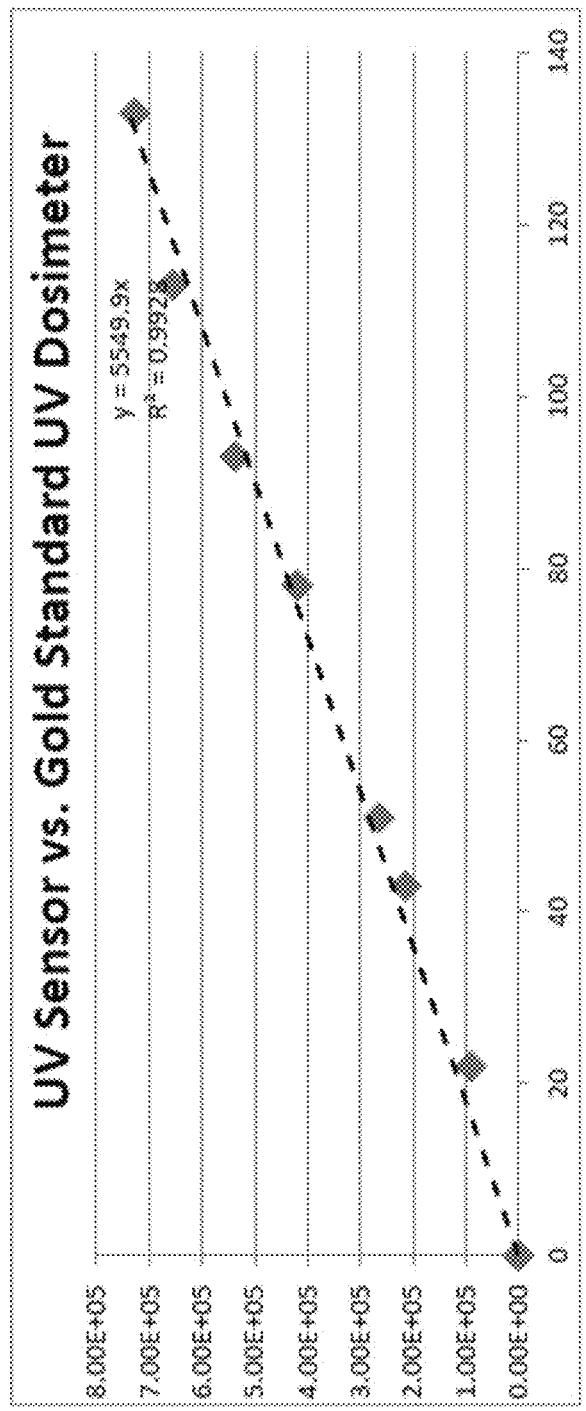
FIGS. 5A-5C shows graphs of UV sensor Measurement under sunlight and with a simulator according to an embodiment.
Figure 5B:
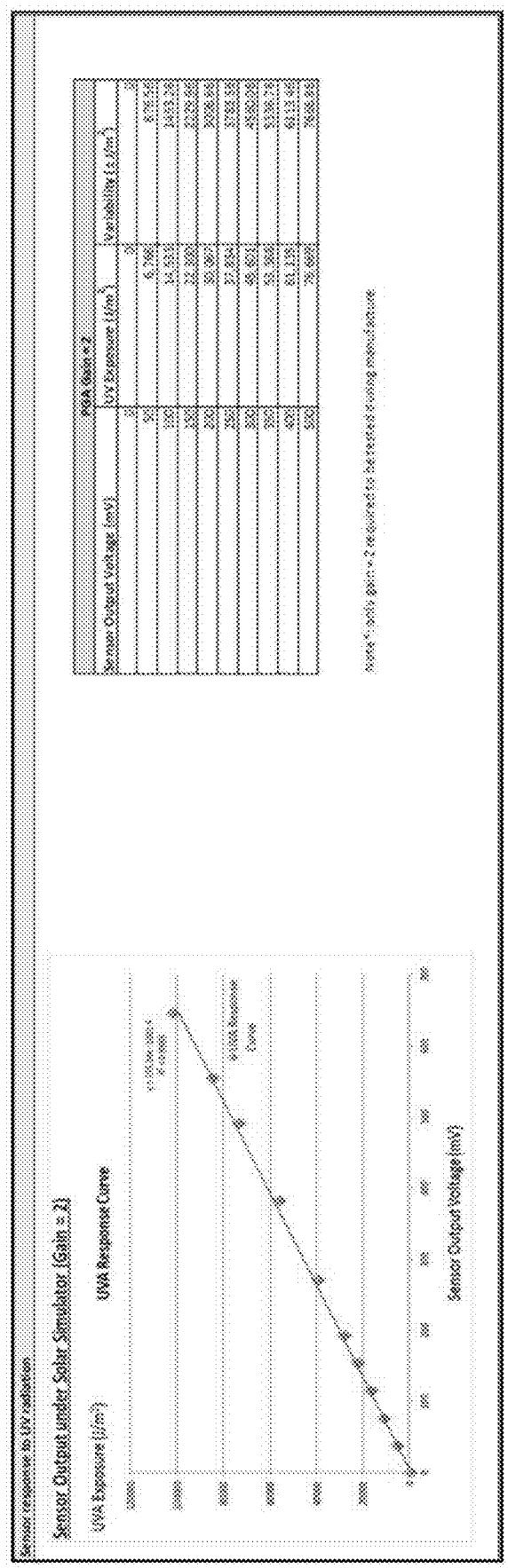
Figure 5C:
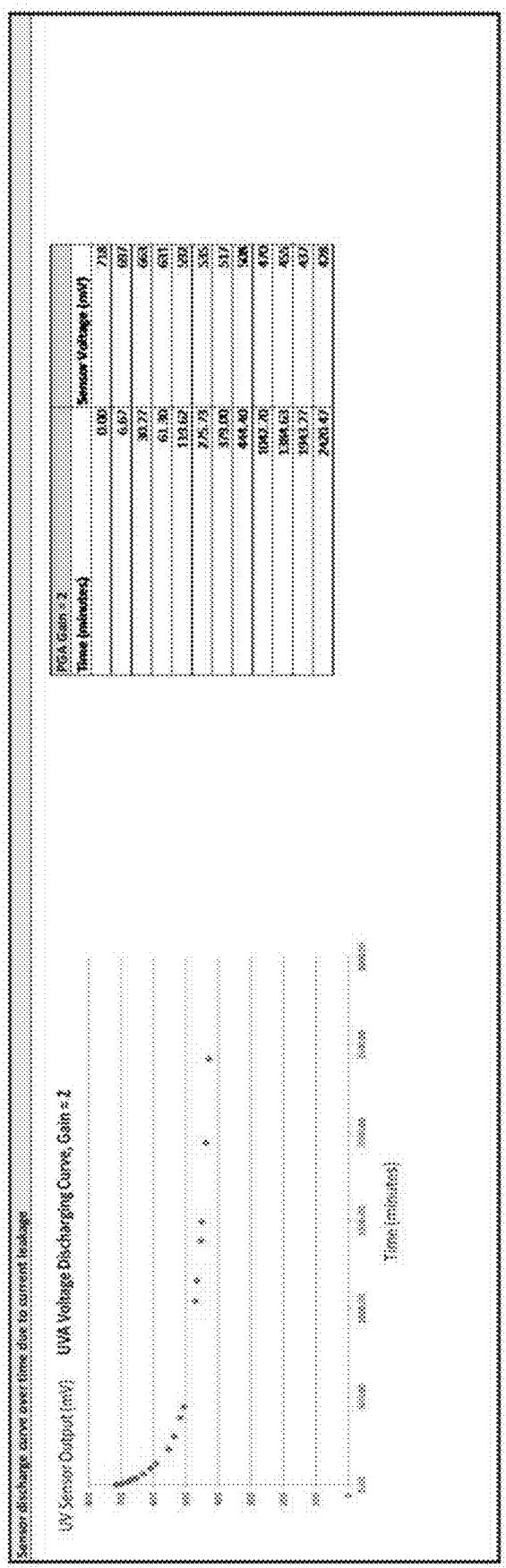

FIGS. 5A-5C shows graphs of UV sensor Measurement under sunlight and with a simulator.

Figure 6:
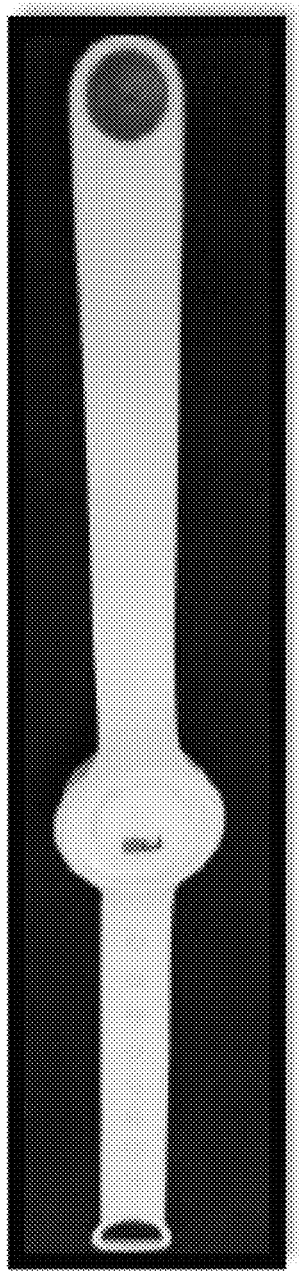
FIG. 6 shows an alternative version of the UV sensor in wrist band format according to an embodiment.
Figure 7A:
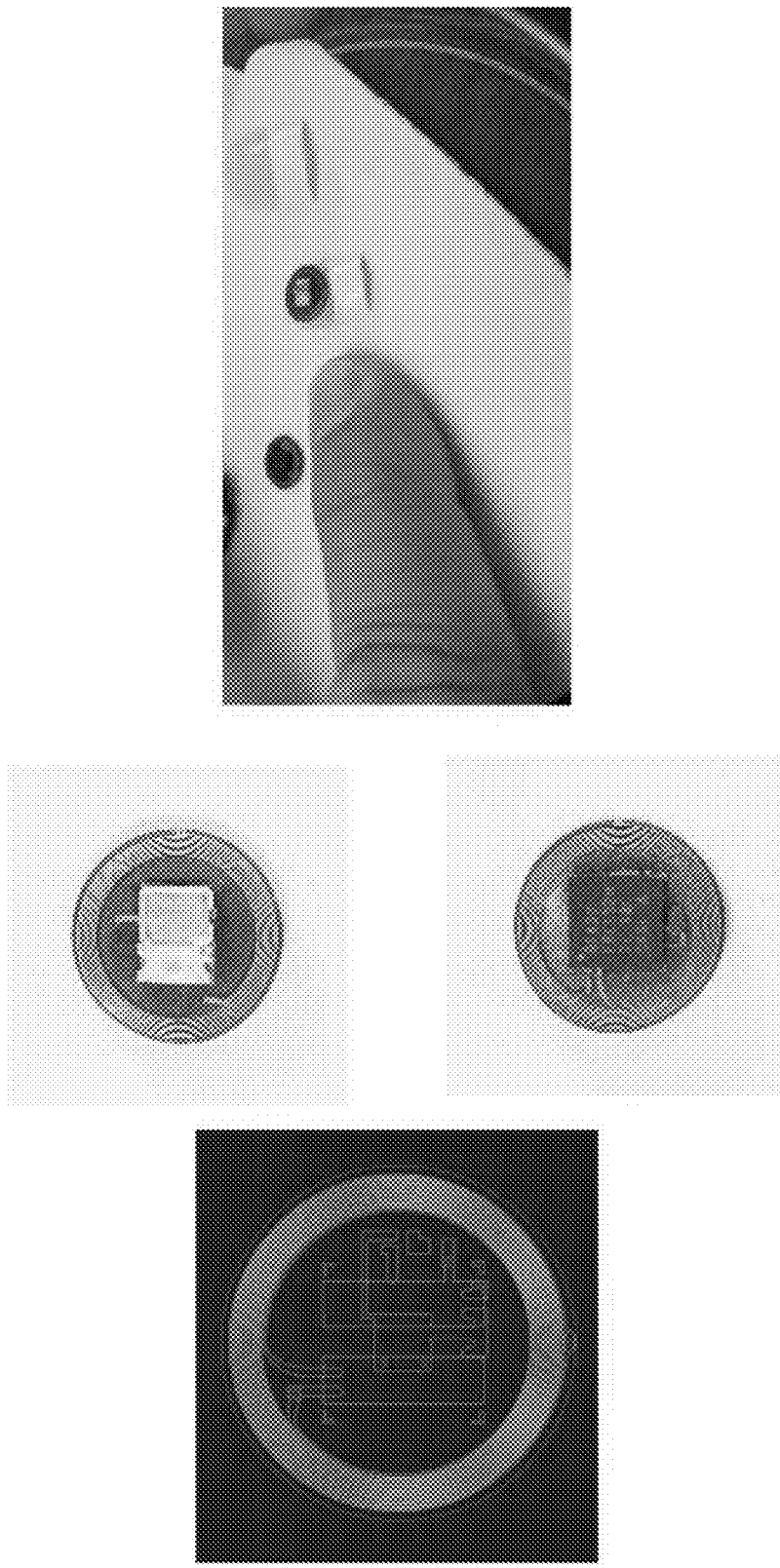

FIG. 6 shows an alternative version of the UV sensor in wrist band format. The specification for this version may be as follows:
- Device consisting of a two layer near field communication device with a Texas Instruments NFC packaged chip
- loop antenna (Cu, ~18 μm thick, diameter: 16 mm, width: 75 μm)
- polyimide film (PI, 18 μm thick) UVA diode as a photo-detector
- Super capacitors
- Device encapsulated with a white dye polydimethylsiloxane
- Device molded in commercial silcone colored bands FIGS. 7A-7B show yet another alternative version of the UV sensor that is configured to be attached to a surface of user's fingernail. The specification for this version may be as follows:
- UVA/UVB Ring device with different sizes
- UVA fingernail sensor with packaged chip
- Device consisting of a two layer near field communication device with a Texas Instruments NFC packaged chip
- loop antenna (Cu, ~18 μm thick, diameter: 16 mm, width: 75 μm)
- polyimide film (PI, 18 μm thick) UVA diode as a photo-detector
- Super capacitors FIG. 7B shows dimensions of the fingernail embodiment (such as 9 mm horizontal and 2.2 mm vertical), along with the relative location of the sensor with respect to the overall accessory. FIG. 7B also shows that a curved adhesive element may be used to attach the accessory to the fingernail.

Figure 8A:
FIG. 8A shows an alternative version of the UV sensor that is configured to be worn on a user's finger as a ring according to an embodiment.

FIG. 8A shows yet another alternative version of the UV sensor that is configured to be worn on a user's finger as a ring. The configuration of the ring version is similar to the fingernail version but it will be placed on ring-shaped band.

Figure 8C:
Figure 8D:

FIGS. 8B-8D shows yet other alternative versions of the UV sensor as a clip, charm, bracelet, or attachment to sunglasses or a wristwatch.

The table below provides additional details regarding an implementation of the sensor.

| SENSOR PART | |
| --- | --- |
| Industrial design (shape) | Needs to be finalized, but see ID documentation for initial concepts |
| Dimensions | 9 mm × 2 mm |
| Weight | xxx gram max (TBD) |
| Colors | Transparent Encapsulation + Colors on the liner |
| Mechanical | Flexible or not (TBD) |
| Encapsulation Material | UV transmitting: specs (TBD) |
| Communication Protocol | NFC ISO 15693 |
| Communication requirements | Based on NFC coil impedance/response to different active devices |

| PGA Gain Setting | | | | |
| --- | --- | --- | --- | --- |
| | 1 | 2 | 4 | 8 |
| Sensitivity (UV Dosage per mV) | 0.0003 MJ/m$^2$ | 0.000150 MJ/m$^2$ | 0.000075 MJ/m$^2$ | 0.000038 MJ/m$^2$ |
| Range (Max UV Dosage) | 0.09 MJ/m$^2$ | 0.09 MJ/m$^2$ | 0.0675 MJ/m$^2$ | 0.0342 MJ/m$^2$ |

| | |
| --- | --- |
| Variability | ±10% for sensitivity and range |
| UV Risk Safe Zone | <1500 J/m$^2$/hour for Skin Phototype 1 |
| Viewing angle | 130°? (Require laser UV light to measure the responsivity of UV LED, discussing with Lime Lab) |
| PCBA BOM | See PCBA tab |

| ATTACHMENT PART | |
| --- | --- |
| Versions | Nail version    Accessory version |
| Application steps | Can be applied, removed and reapplied |
| Application duration | Min 24 hours |
| Application cycles | Min 10 times |
| Product definition ideas | 1. Initial state: sensor with adhesive at the bottom + separate accessory -> sensor can be applied on nail or on accessory and removed from both<br>2. Initial state: sensor with adhesive at the bottom + separate accessory -> can be attached to nail and removed or on accessory but unremovable from accessory once attached<br>3. Initial state: sensor attached to accessory (no nail attachment) |

FIGS. 9A-9D show examples of displays shown on an application that is executed on client device 102 (such as a smartphone). The UV sensor detects UV exposure and transmits the detection data to the client device. In one example, the UV sensor transmits sensed data multiple times at regular intervals (for example, every two hours) through the day. As shown in FIGS. 9A-9C, the application display on the client device 102 may provide an indication of the user risk level in percentage form, along with a category label such as "low", "moderate," or "high." Additionally, other pieces of information may be displayed as shown in FIGS. 9A-9C, such as location, current humidity, UV index, current temperature, pollen level, and air quality. A graph may also be displayed that tracks the UV exposure level over time for the day, and it may include further information taken from a user's schedule (such as "afternoon run"). The display may also show a message based on the risk level, such as a congratulatory message ("well done") or a caution message ("Caution: your UV exposure increase 39% in the past hour"). As shown in FIG. 9D, there may be a display that shows both UVA and UVB exposure.

FIGS. 9E-9G show examples of the application display based on a daily display, a weekly display, or a monthly display.

FIG. 9H shows a display on the application, in which a user may manually perform synchronization operation (by tapping on a user interface element) to obtain the latest UV sensor data from the UV sensor.

FIG. 9I shows a display on the application which shows the user profile, which may include items such as name, birthdate, gender, skin tone, skin type, and the type of sunscreen currently used.

FIG. 9J shows a display on the application which shows user activities and the amount of sessions and average UV exposure incurred for each activity.

FIG. 9K shows a display on the application which includes more details for one of the activities (such as running). The details will include the actual UV exposure incurred for each individual session.

The UV Sense App (application) has been developed for Clinical Study and Evaluation purposes. The app allows the researchers to setup the parameters for sensors and user alerts. The data can be uploaded to the cloud server(s) immediately for real-time evaluation of the studies.

Figure 10B:
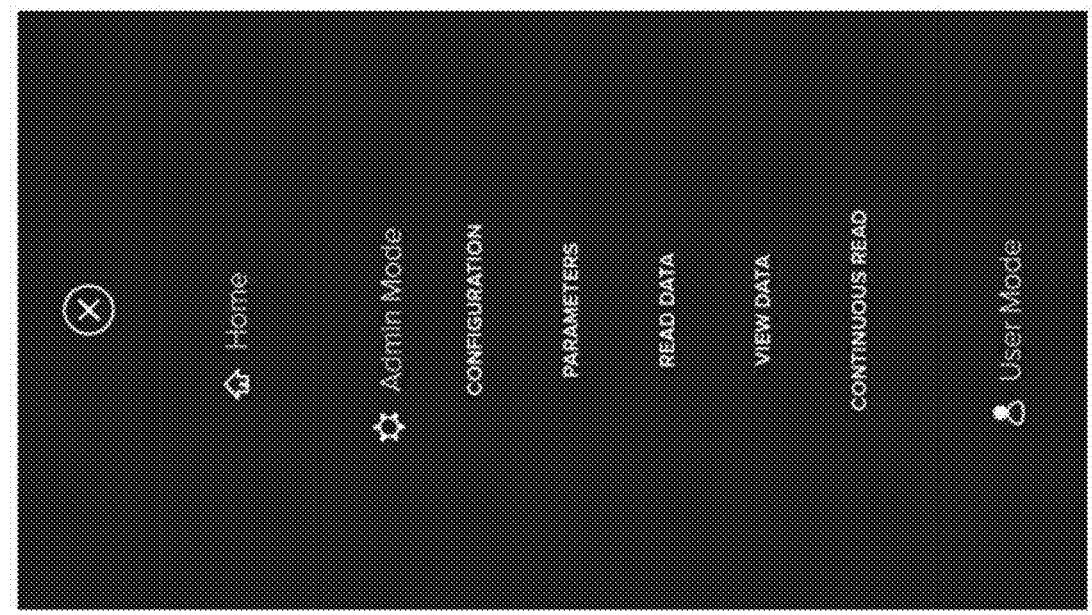
FIGS. 10A-10J show additional examples of displays shown on an application that is executed on a client device according to embodiments.
Figure 10A:
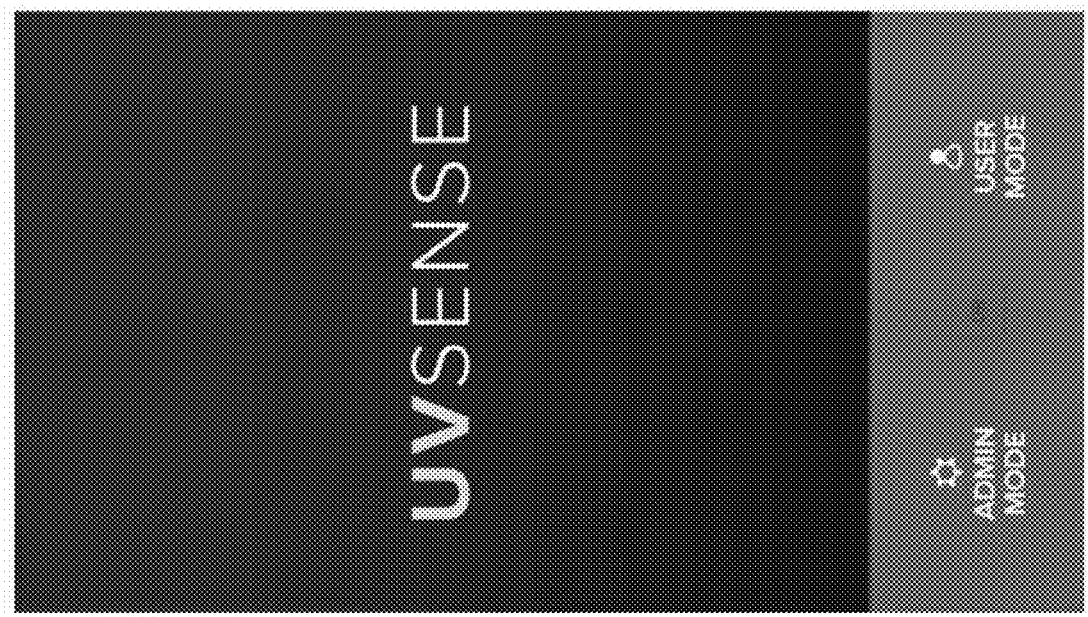

FIG. 10A shows a login page for the first interface of the app. The researchers can select Admin Mode and login with password, while users will select User Mode for taking data only.

FIG. 10B shows that in the Admin Mode, there are five sections,
 1. Configuration: setting up sensor information and subject data
 2. Parameters: setting up parameters for converting electronic charge into UV exposure
 3. Read Rata: Read the data from sensor and reset the memory 4. View Data: Select data set to display in table of graphs 5. Continuous Read: Read data in a set sampling rate, for calibration purposes.

FIGS. 9-10 shows that an Admin Configuration Section, which includes:

Patch ID: Enter Patch information (eg. Left Arm LA). The information can be written to the RFID chip, so the patch can be recognized again during Data Reading Subject ID: Enter subject ID (eg. 001) for the study. The information will be written to the RFID chip, so the patch can be recognized with the subject PGA Gain: Sensitivity setting, written to the memory of the RFID chip Reset Time: Time required for users to hold the phone above the device for resetting the data User Alert Interval: Time (in minutes) for alerting user to take data again.

Figure 10D:
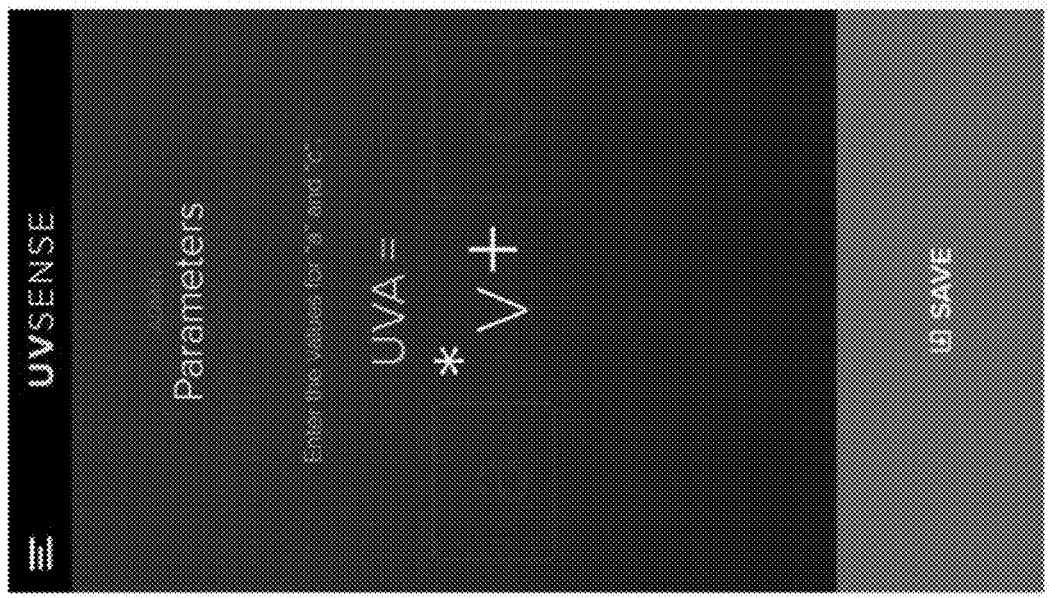
Figure 10C:
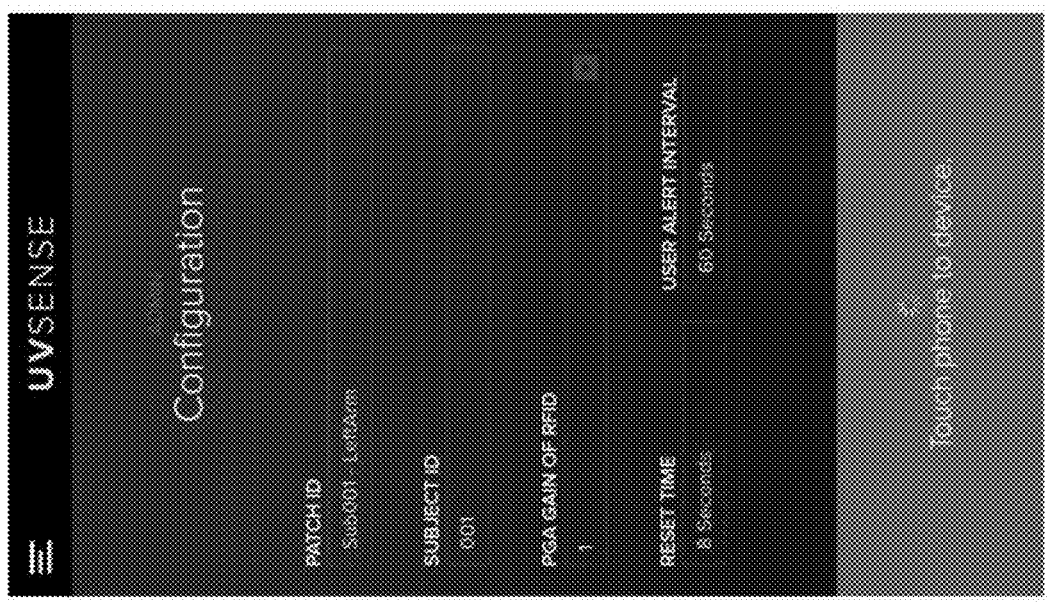
Figure 10F:
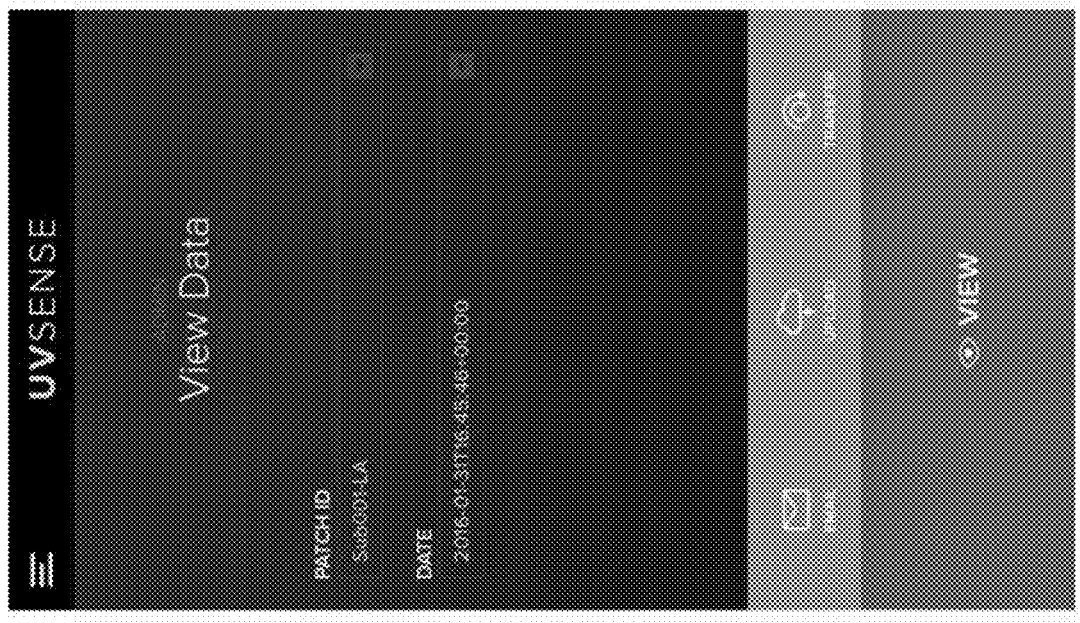
Figure 10E:
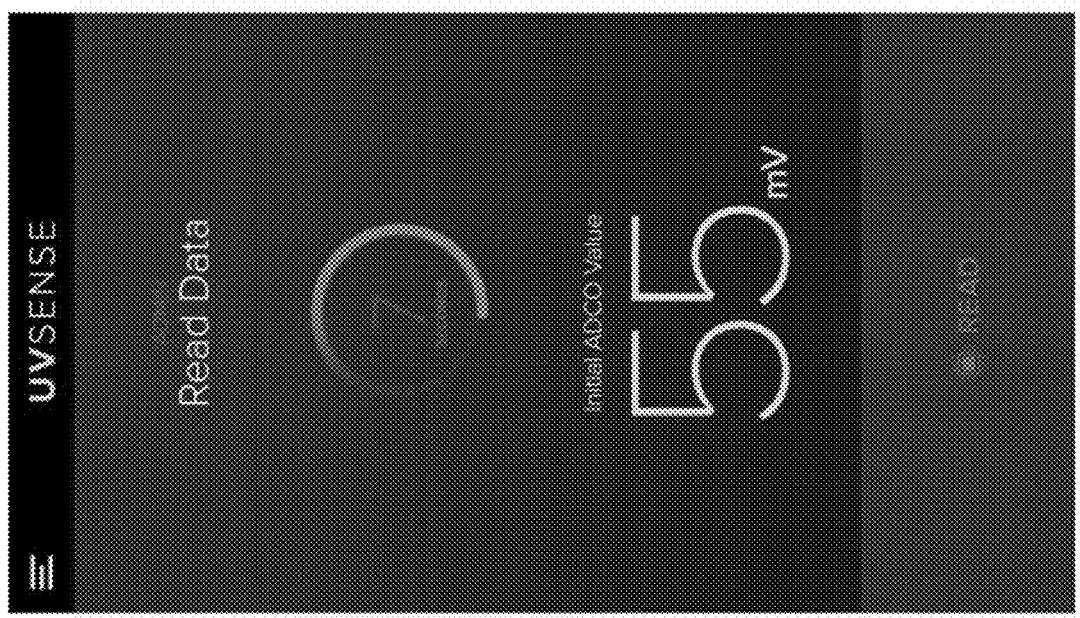

FIG. 10D shows that an Admin Parameters section, which allows for setting up parameters for converting stored electronic charges into UVA Exposure FIG. 10E shows an Admin Read Data section, which includes the following features:

It will ask user to press read data and start looking for the device. Once the device is found, an initial reading will be taken while counting down with preset resetting time. At the end of the reset period, another final reading will be taken.

In the User Mode, there will be no values displayed. Only counting down clock is present to notify users holding the phone above the device.

FIG. 10F shows an Admin View Data section, which includes an interface for selecting the patch ID and date. The data is organized into different dates, so the researchers can easily browse the data.

Figure 10H:
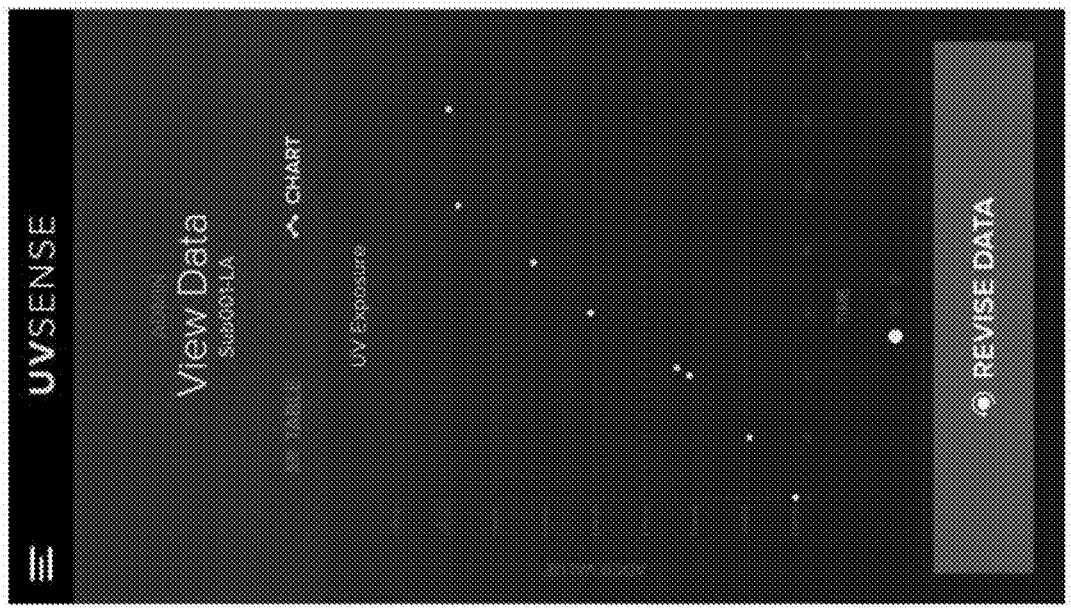
Figure 10G:

FIG. 10G shows a Table which can be accessed from the View Data section. It allows data to be displayed in a table format, organized by time and reading condition.

FIG. 10H shows a graph which can be accessed from the View Data section, where data can be displayed in graph format, showing UV exposure vs. time of measurements, for example.

Figure 10J:
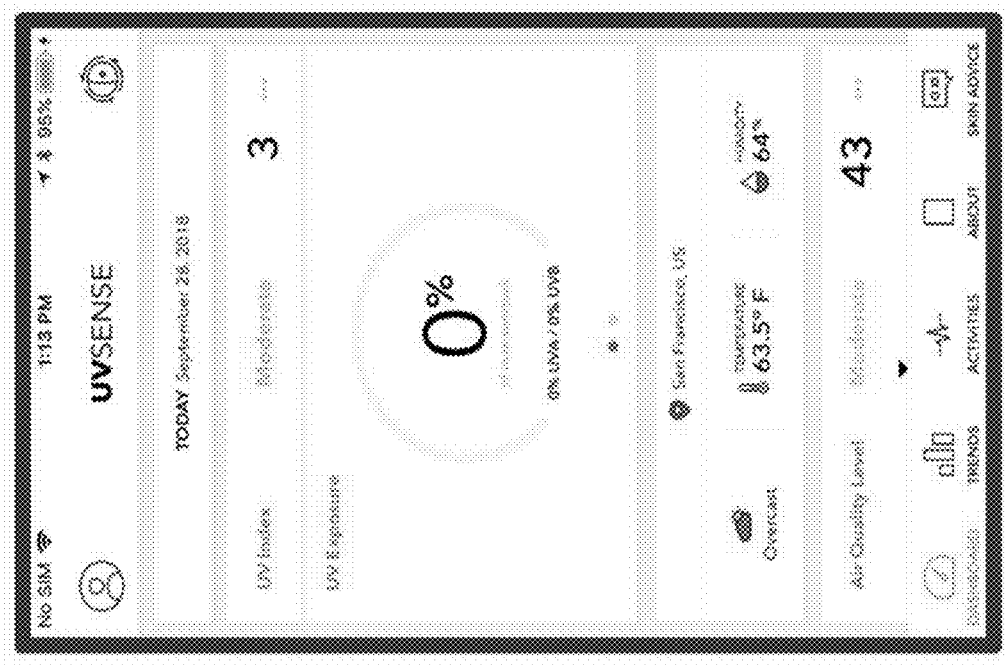
Figure 10I:
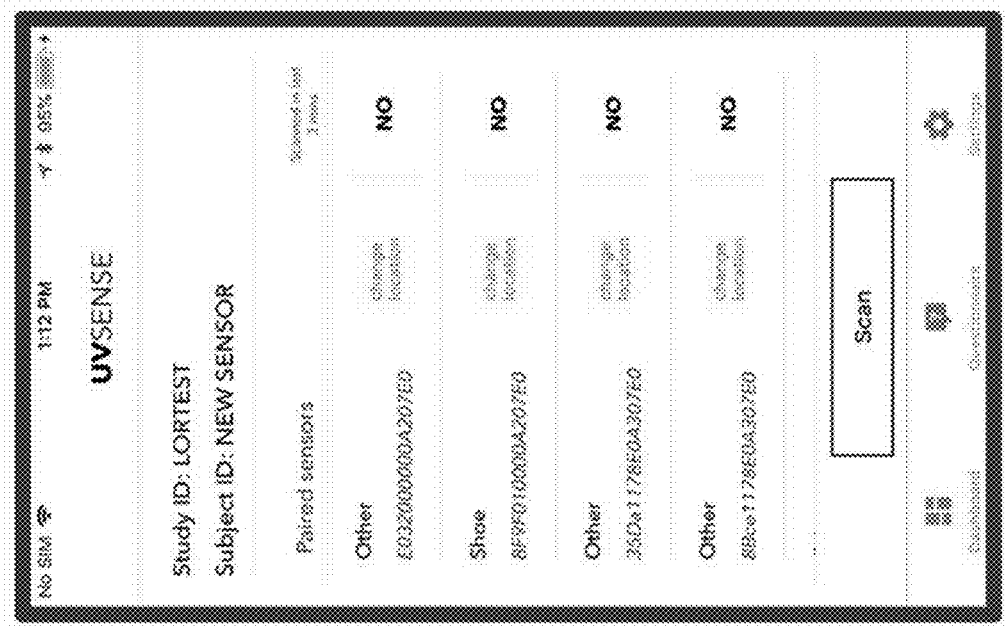

In an embodiment, FIG. 10I shows an application interface which may be used in a clinical research application. The interface show in the figure is based on Apple research kit, and researchers may enter study ID and subject ID. The application clearly displays the sensor IDs and locations and performs tracking of UV data per sensor.

In an embodiment, FIG. 10J shows an application interface which may be used in a consumer application. The application connects with a cloud server for providing consumer data. The application further displays weather, pollen, and UV information; alerts users when reaching daily UV sunstock; computes UVB from UVA and geolocations; and tracks UV exposure per activities.

Figure 11:
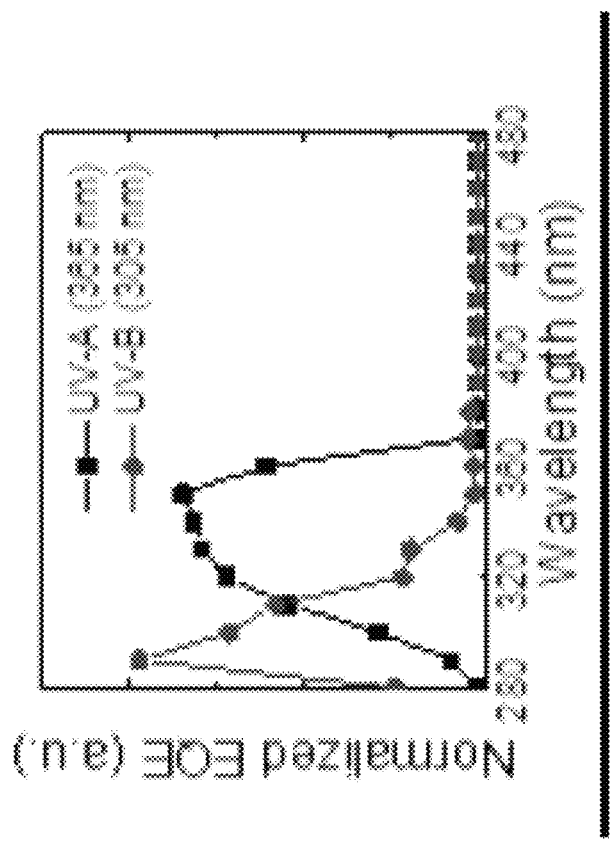
FIGS. 11-14 show different data results for bench calibration/testing of embodiments.
Figure 12:
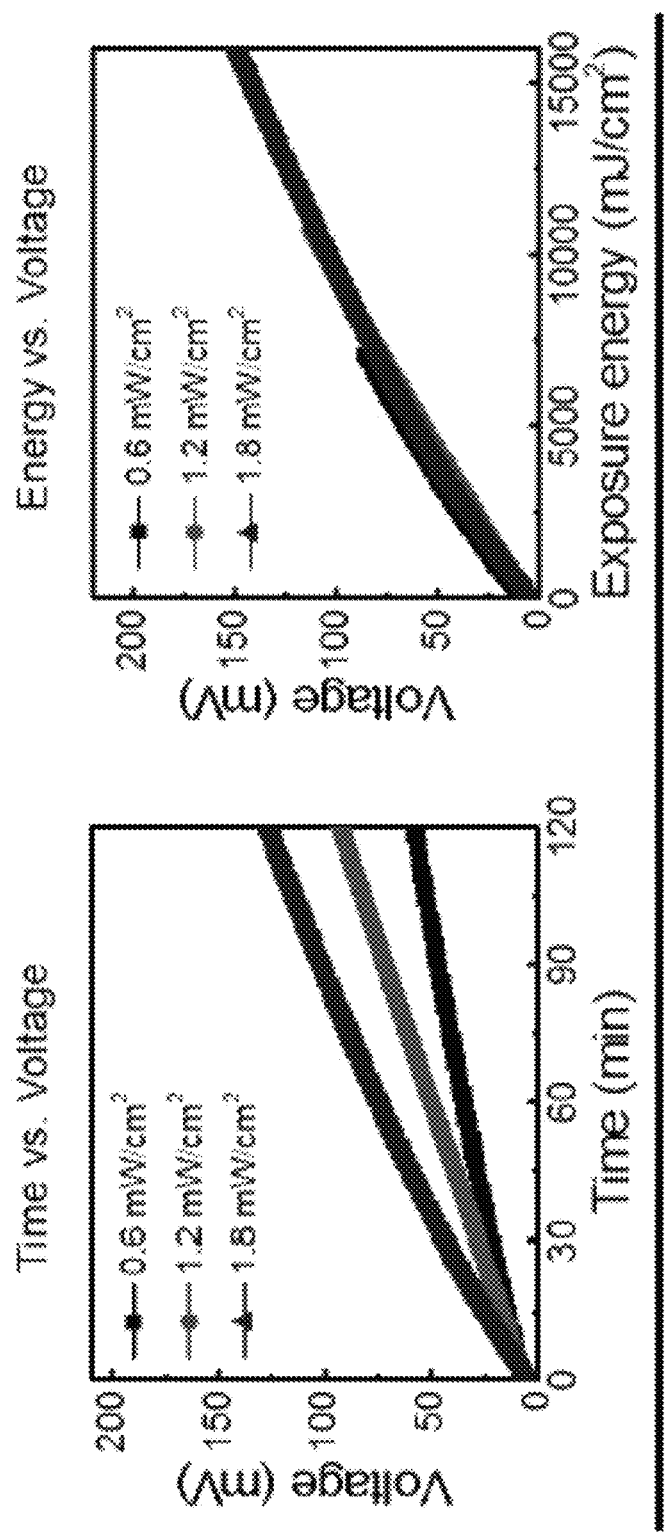
Figure 13:
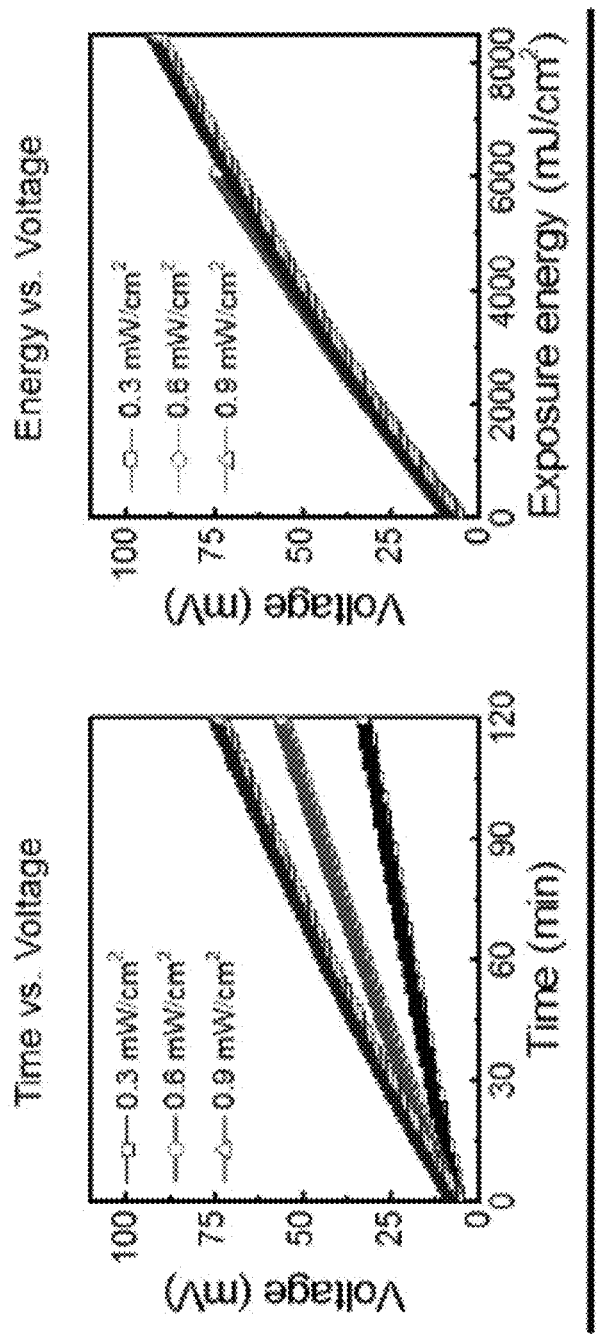
Figure 14:
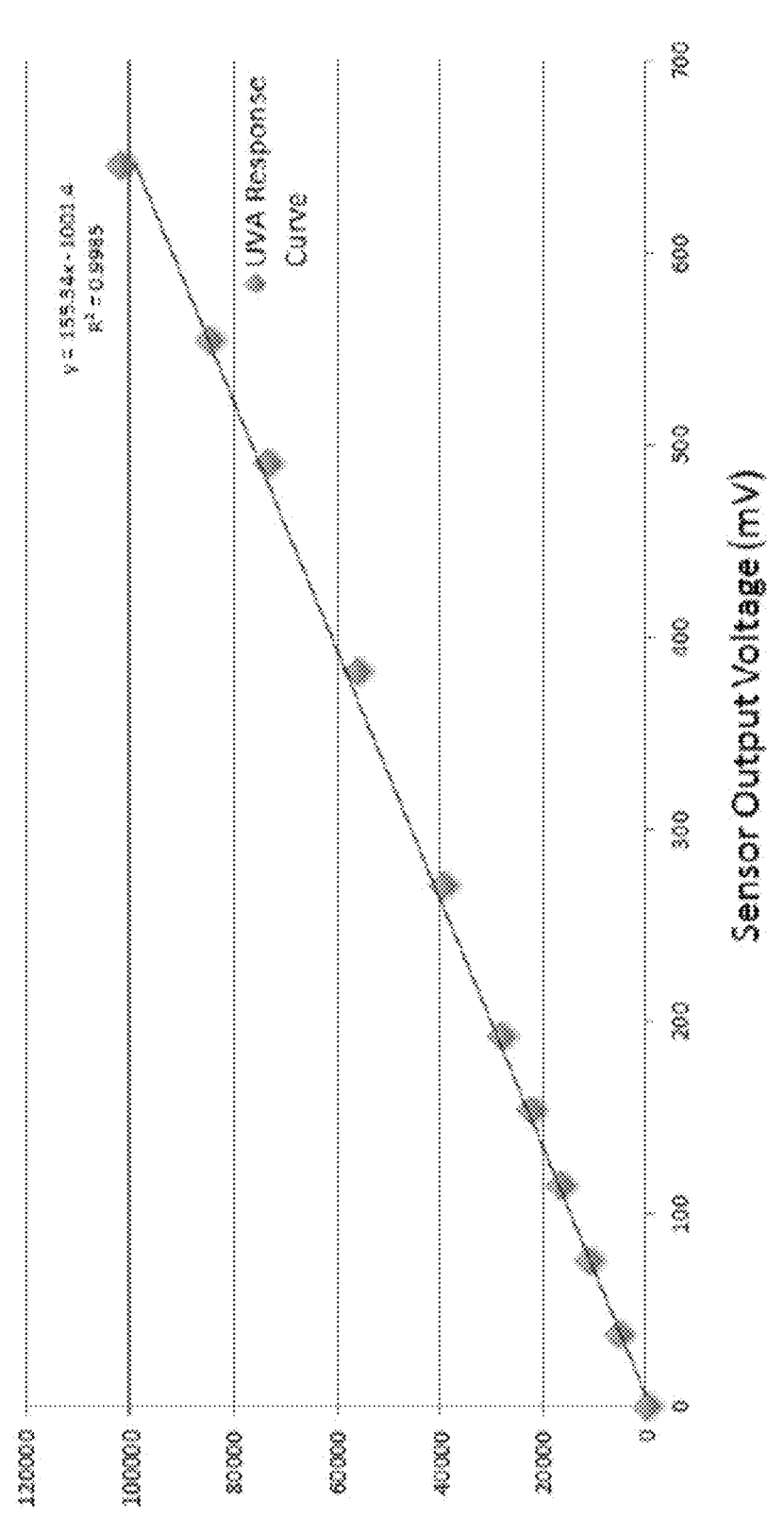

FIGS. 11-14 show different data results for bench calibration/testing. FIG. 11 shows the UVA/UVB detectors external quantum efficiency (EQE) spectrum. FIG. 12 shows UVA response measurements for time vs. voltage and energy vs. voltage for different UVA intensities. FIG. 13 shows UVB response measurements for time vs. voltage and energy vs. voltage for different UVB intensities. FIG. 14 shows the sensor output (based on UVA exposure) in millivolts under a solar simulator with a gain of 2.

Figure 15:
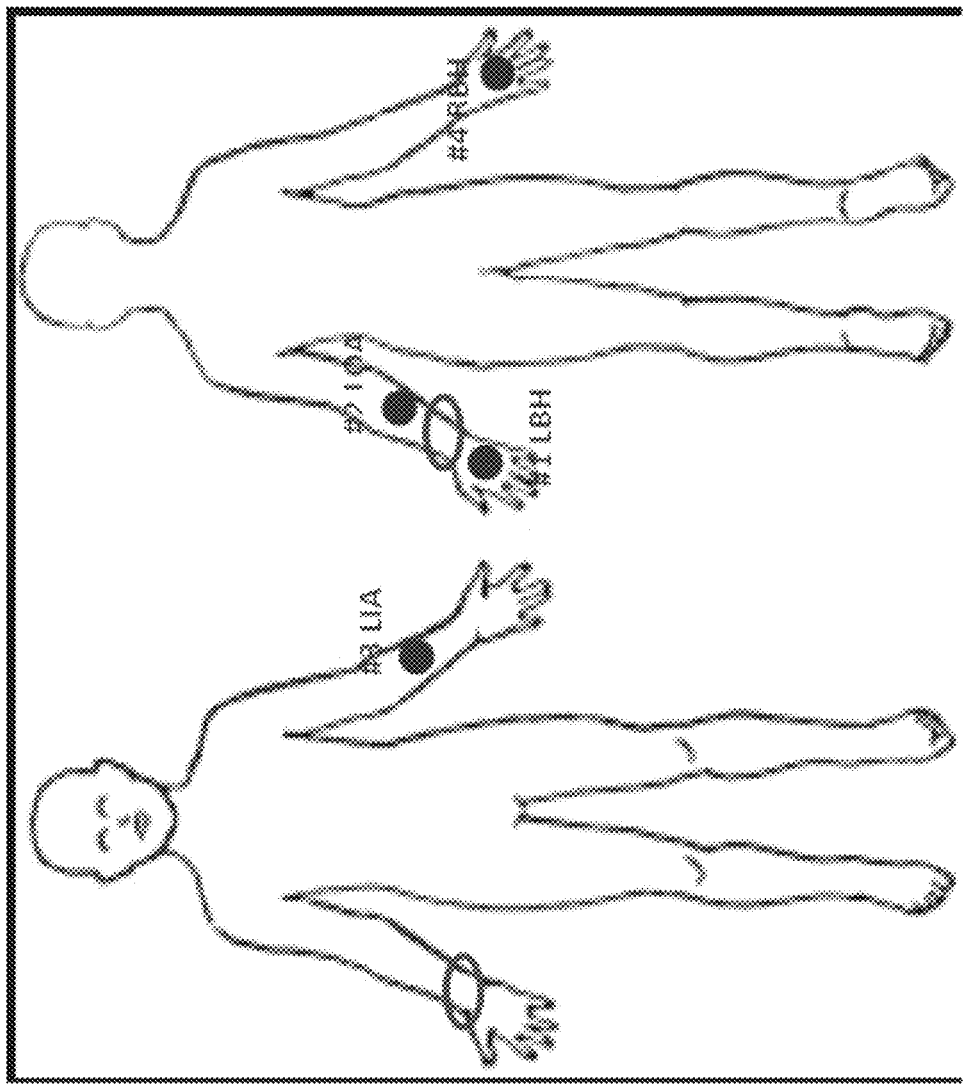
FIG. 15 shows UV sensor placement on the subjects of a clinical study.
Figure 16:
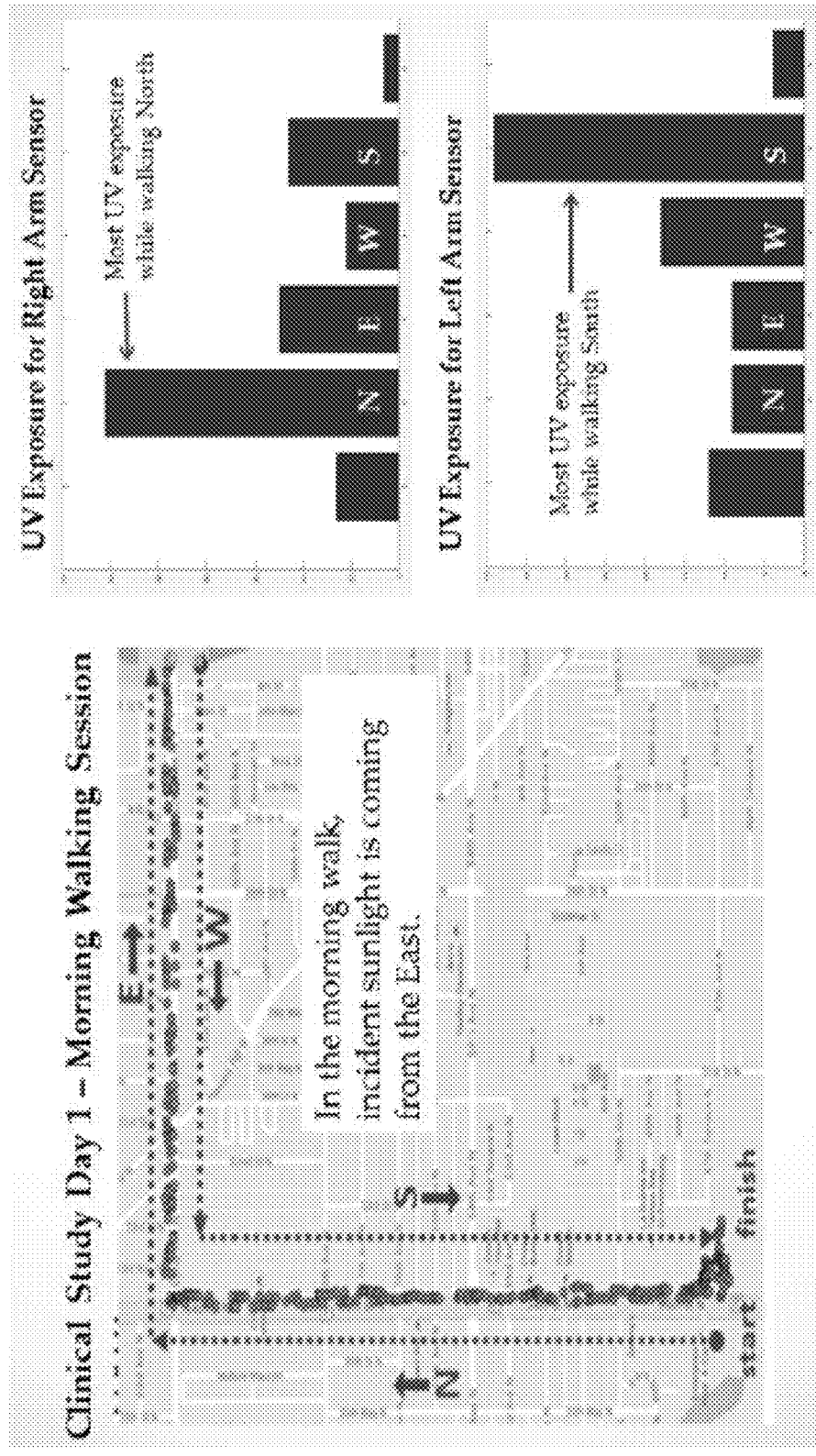
FIGS. 16-21 show the results of the clinical study evaluation using the UVA/UVB sensor(s) with certain parameters and conditions.
Figure 17:
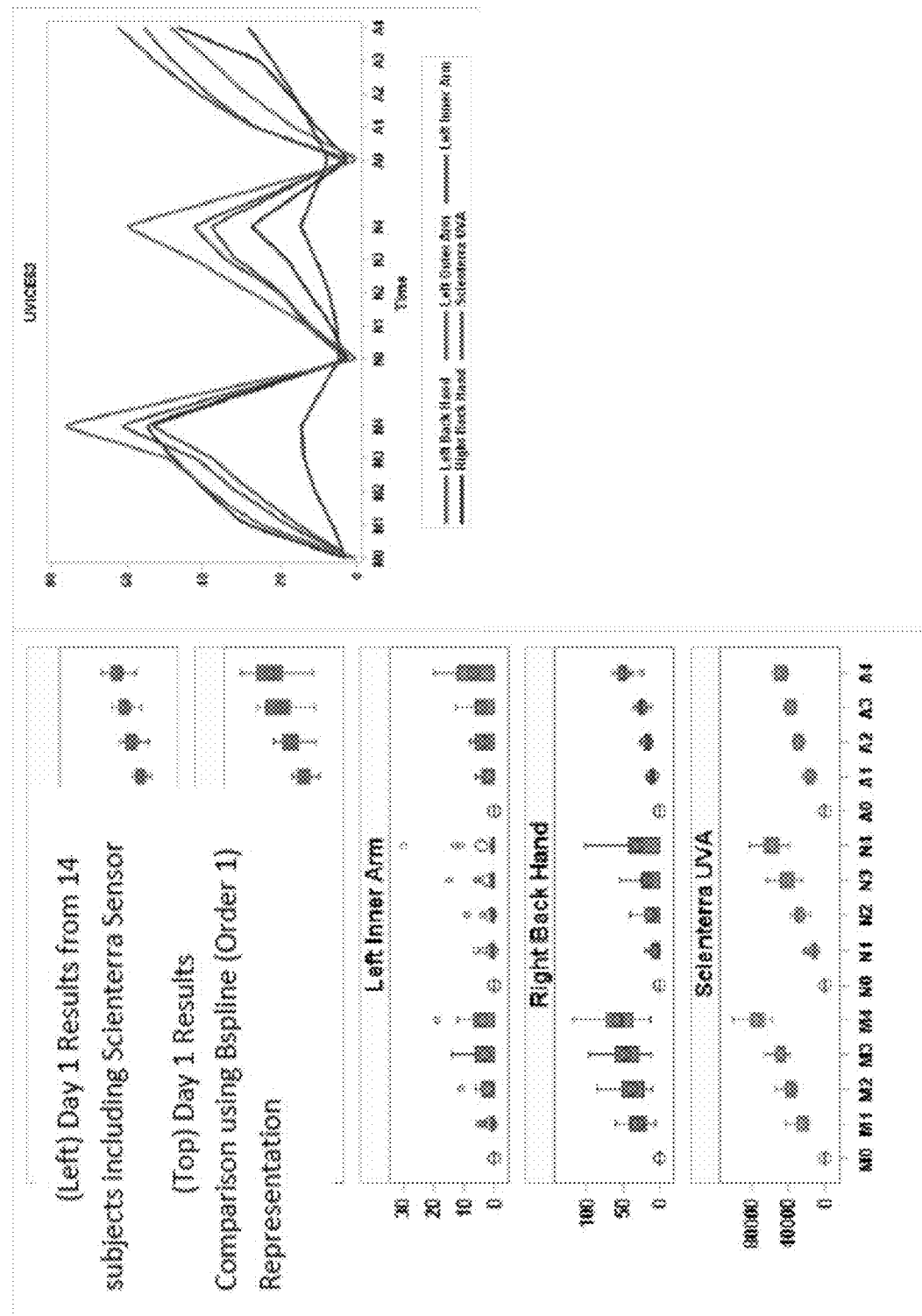
Figure 18A:
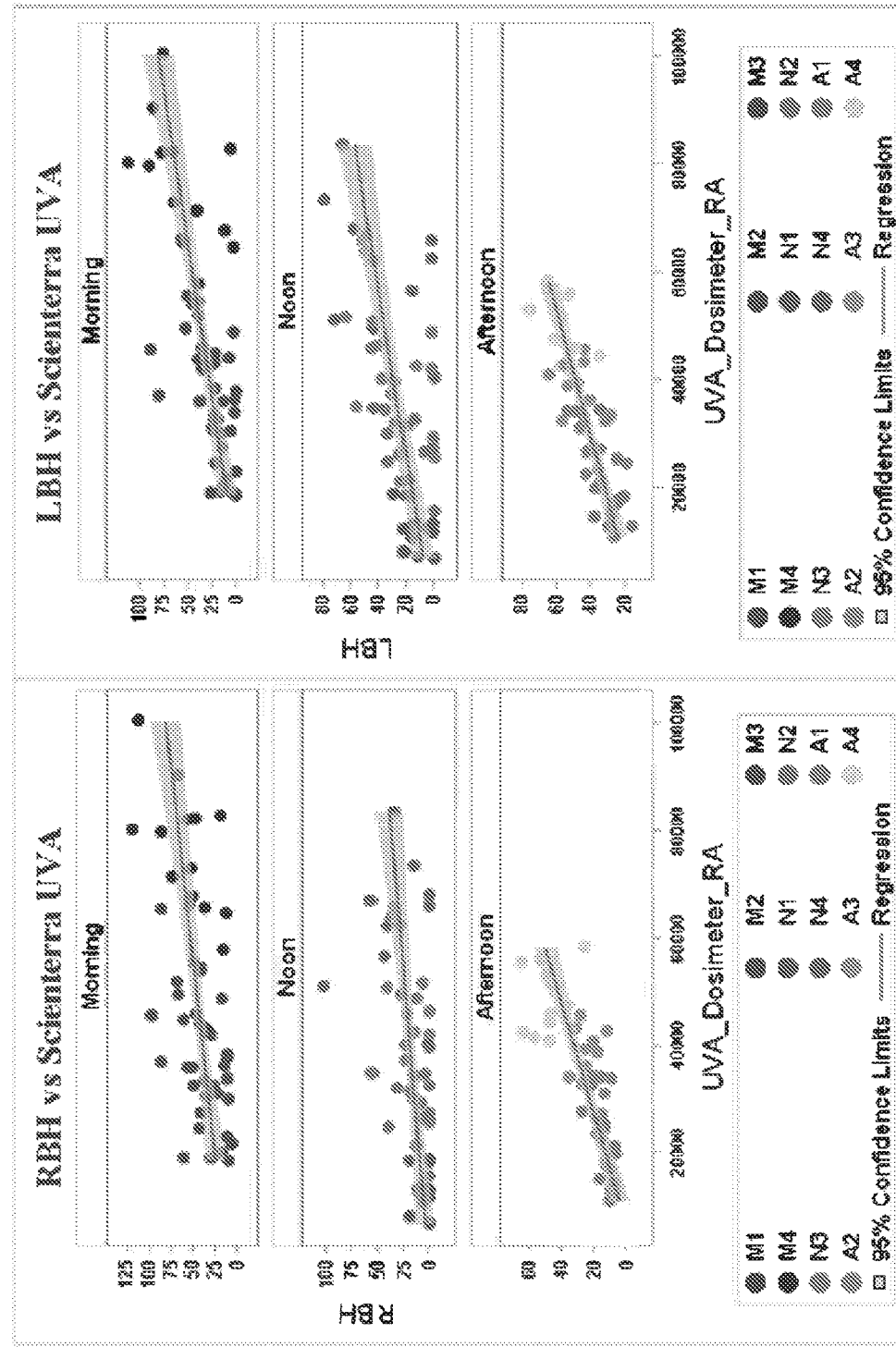
Figure 19:
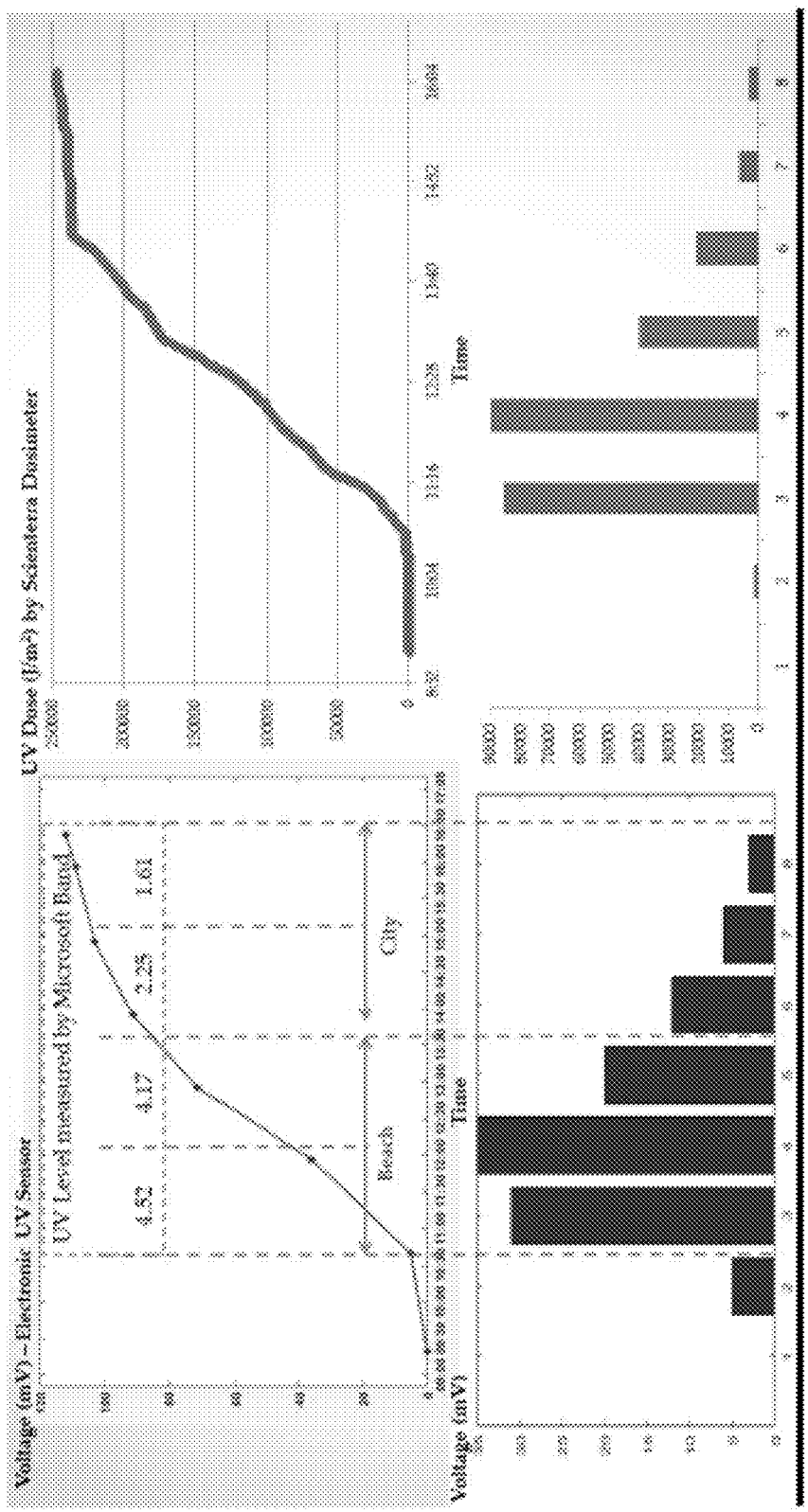
Figure 20:
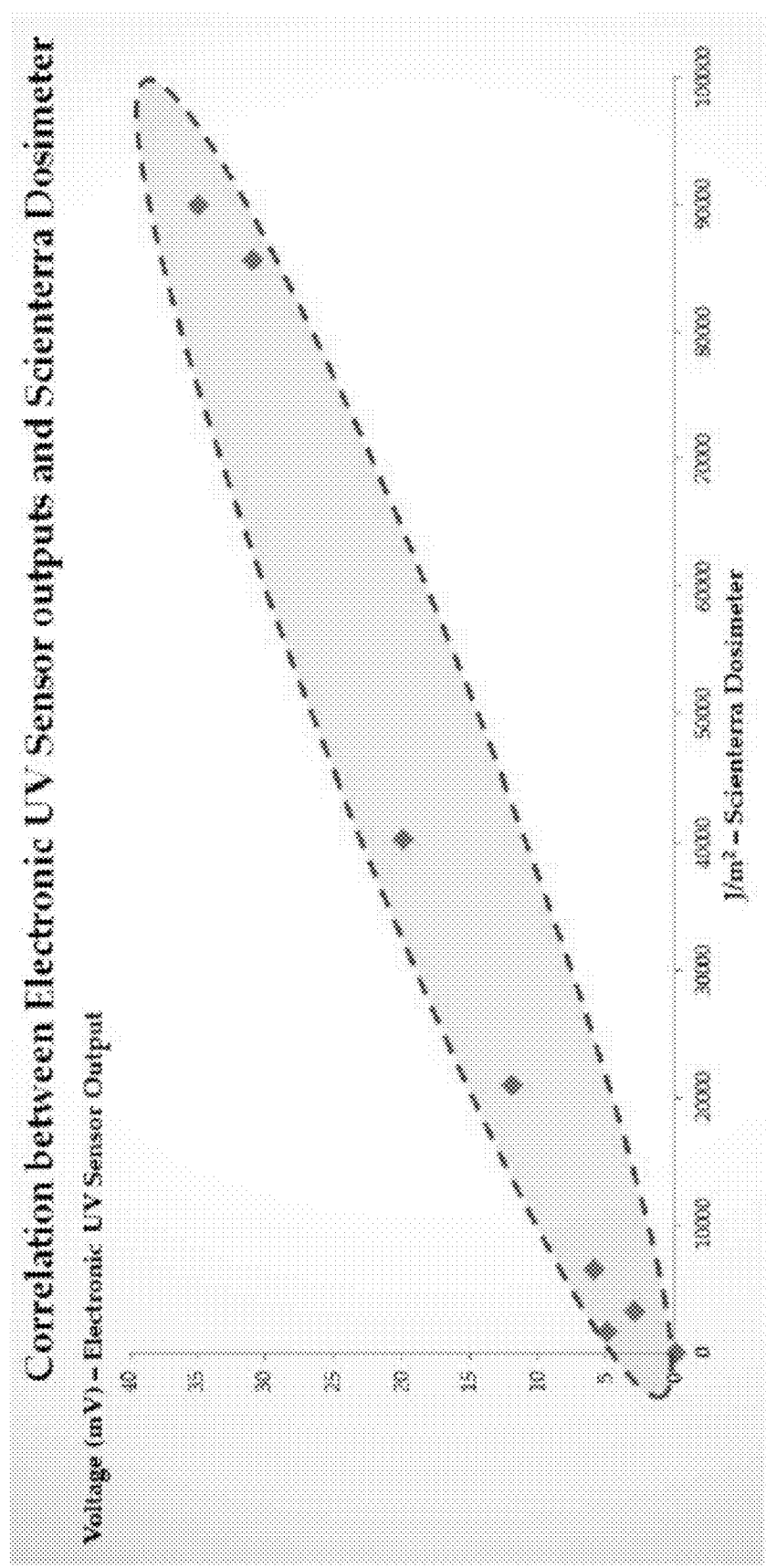
Figure 21:
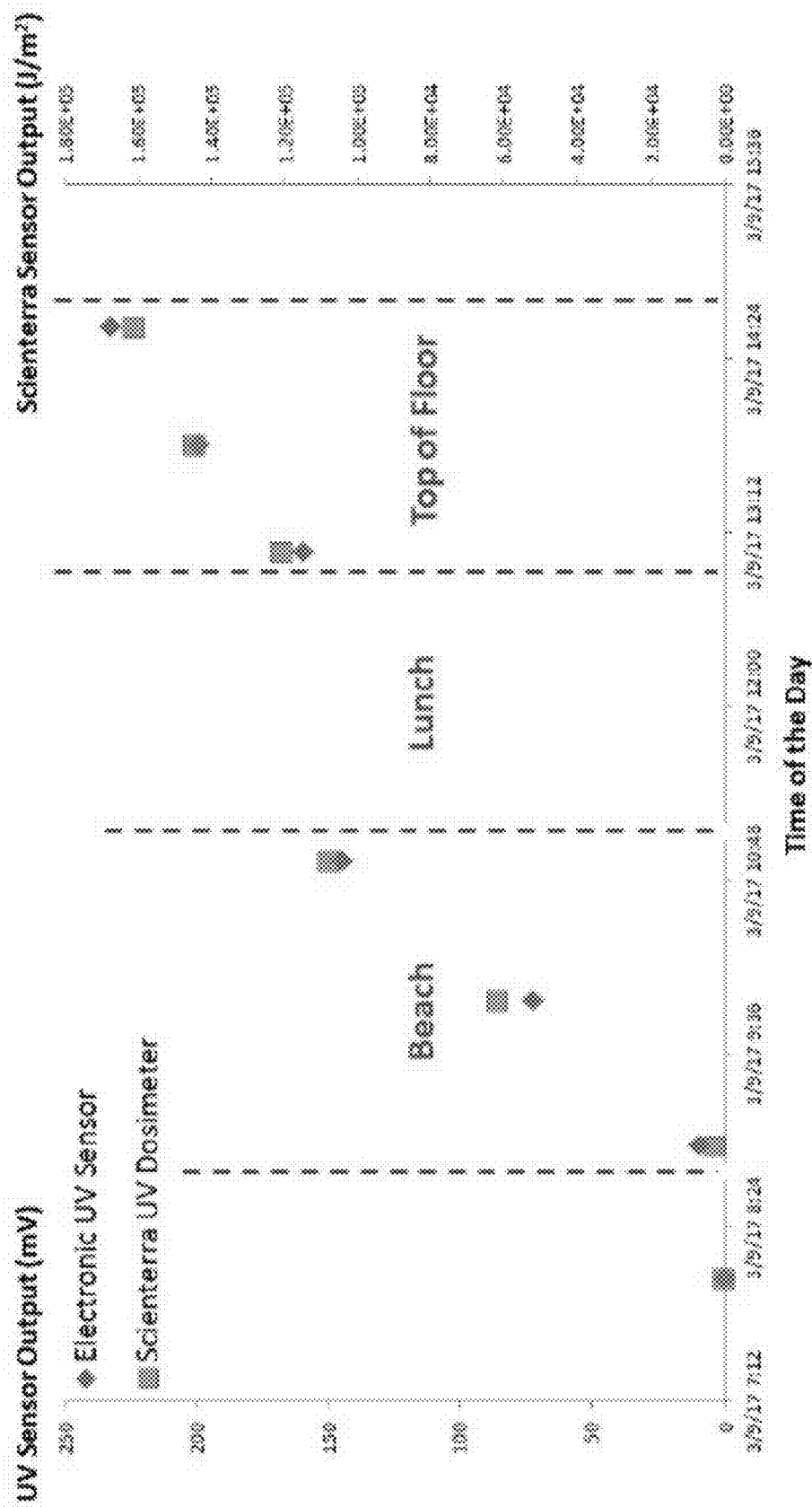

FIG. 15 shows UV sensor placement on the subjects of a clinical study that compares the performance of the wearable UV sensor described in the present embodiments with a reference device, such as electronic Scienterra UV dosimeters. FIGS. 16-21 show the results of the clinical study evaluation using the UVA/UVB sensor(s) with the following parameters and conditions:

Date: September 2016
Location: Tampa, Fla. USA
Number of Subjects: 14
Number of Sensor per Subject: 4
Sensor Locations: #1 Left Back Hand, #2 Left Outer Arm, #3 Left Inner Arm, #4 Right Back Hand
Days of Study: 4
Day 1: Directional Walk in N, E, W, and S directions
Day 2: Beach and City Comparison
Day 3 & Day 4: Daily Life Activities FIG. 22 shows the preliminary results of the clinical study evaluation using the UVA/UVB sensor(s) with the following parameters and conditions:

Date: March 2017
Location: Rio, Brazil
Number of Subjects: 19
Number of Sensor per Subject: 1
Sensor Locations: Thumb or Middle Finger
Days of Study: 4
Day 1 & 2: Rooftop, normal activities, no water
Day 3: Beach in the morning and rooftop in the afternoon
Day 4: Rooftop, swimming pool activities Alternative Embodiment(s)

Figure 22:
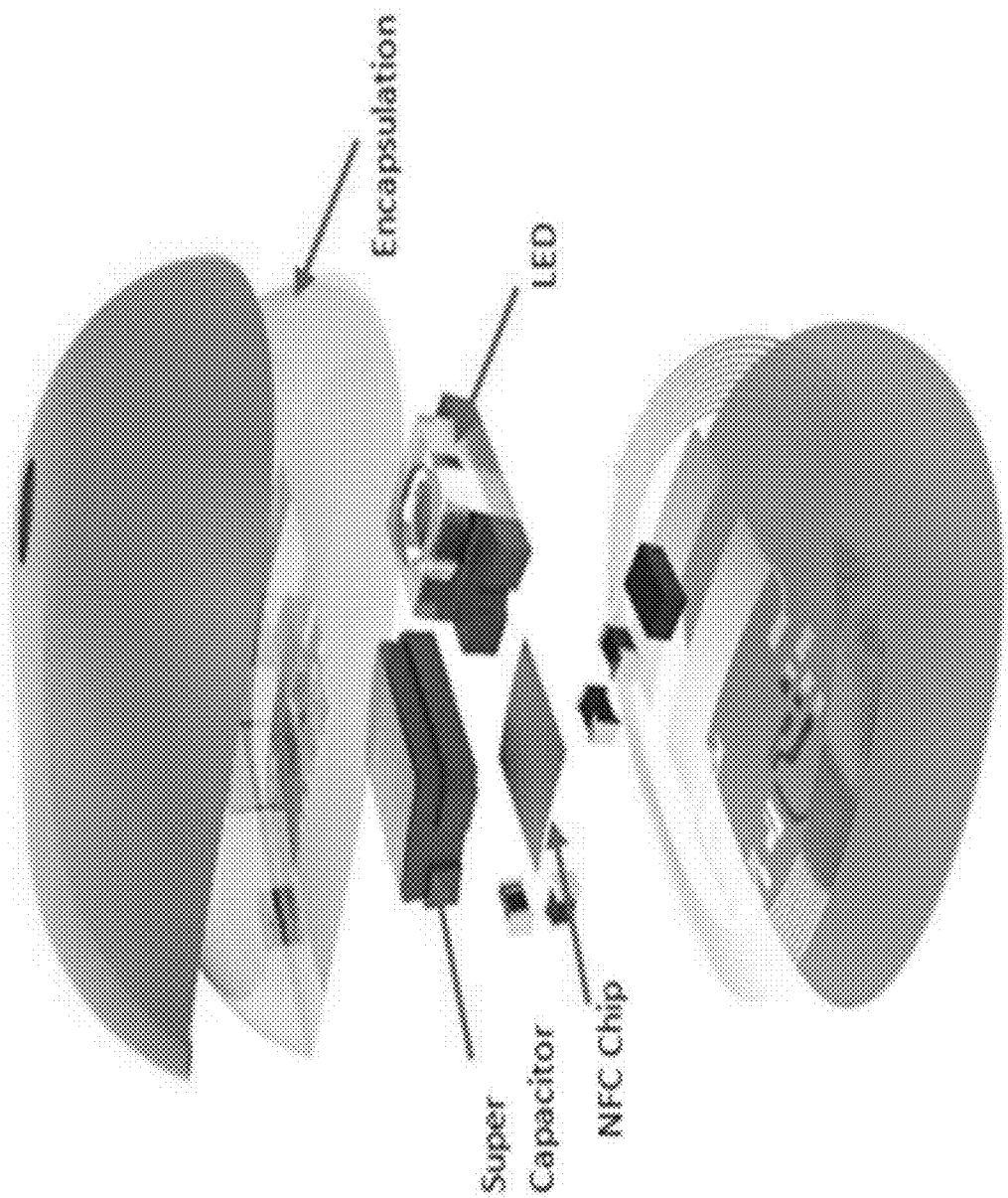
FIG. 22 show the results of the clinical study evaluation using the UVA/UVB sensor(s) with certain parameters and conditions.

The following embodiment describes manufactured sensors with packaged RF430 chips, having the following specifications:

UVA Sensor
UVA Sensing LED in UV Transmitting Acrylic Packaging
Designed Metallic clip to minimize the interference with NFC Antenna
Optimized Schematic Design for Manufacturability FIG. 22 shows an exploded view of the sensor according to this embodiment. As can be seen, the sensor includes an encapsulation layer 2201, an LED 2202, a super capacitor 2203, and an NFC chip 2204.

Figure 23:
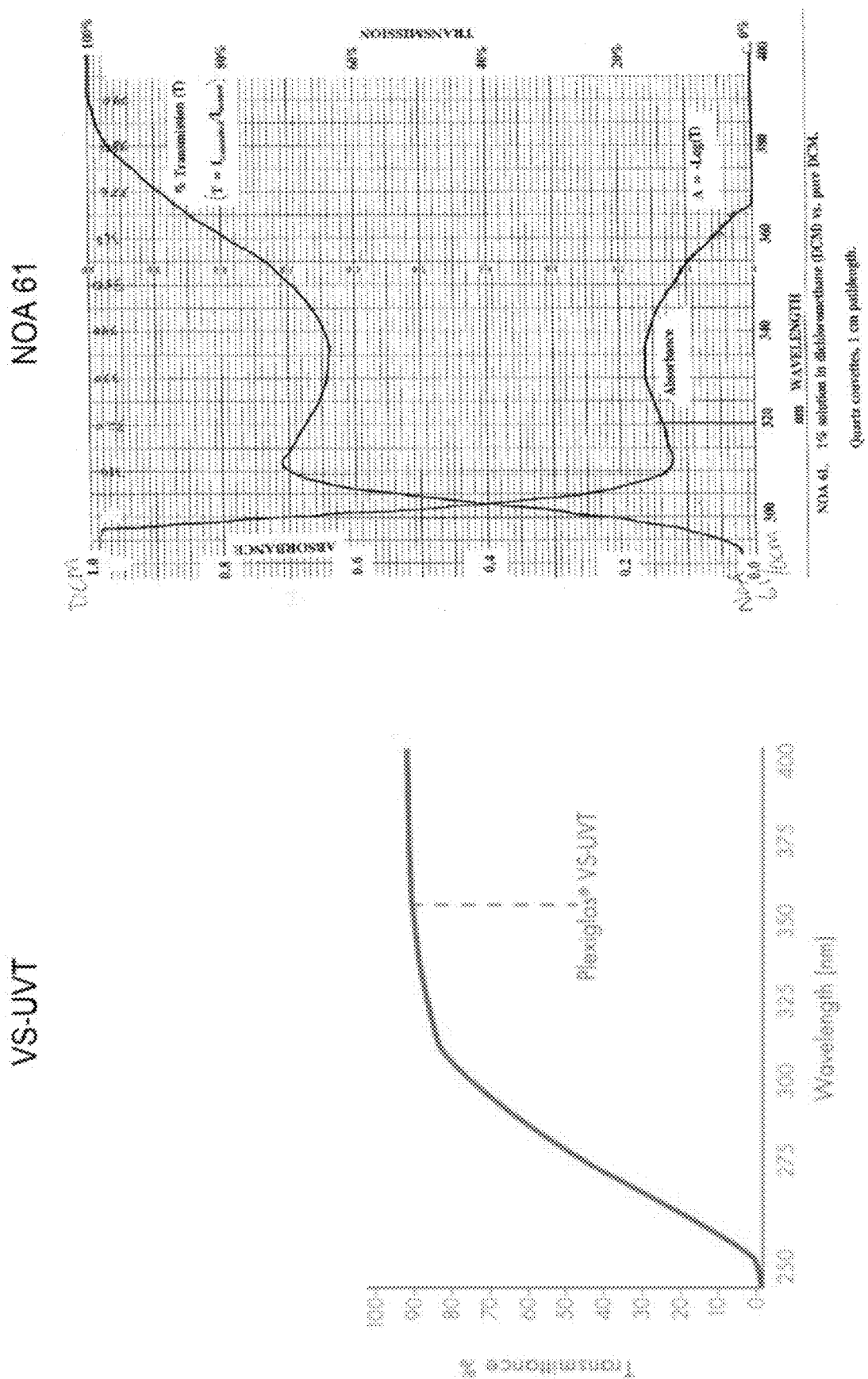
FIG. 23 shows a UV transmission curve for the VS-UVT material.

Additionally, in the embodiment, new encapsulation material (Plexiglas VS-UVT) may be selected to wider pass band range for UV light (300 nm to 400 nm with 90% transmission), comparing to the NOA 61 used in the CES (80% transmission at 360 nm). FIG. 23 shows a UV transmission curve for the VS-UVT material.

Figure 24:
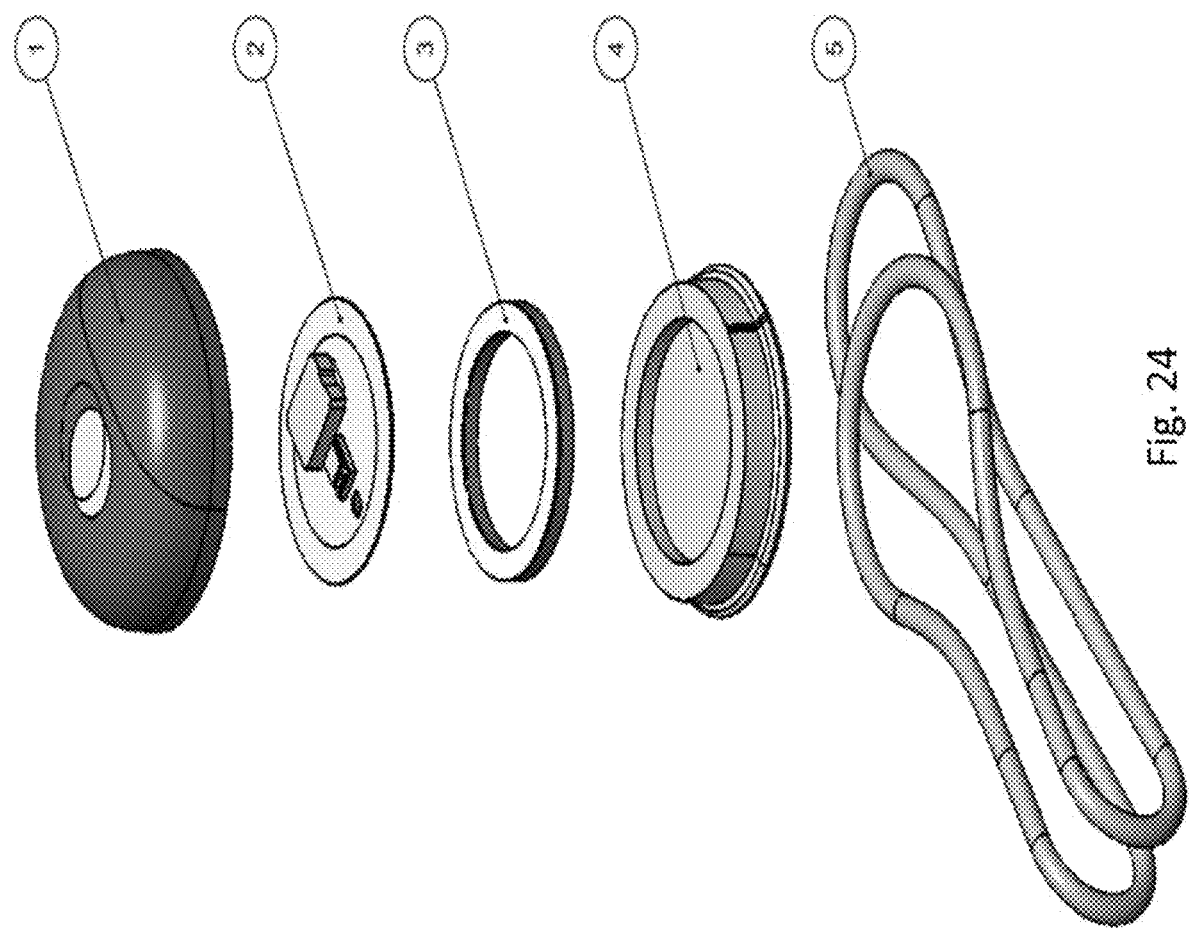
FIG. 24 shows an exploded view of a sensor according to an embodiment with an alternative mechanical clip design.

FIG. 24 shows an exploded view of the sensor according to an embodiment with an alternative mechanical clip design (element 5) with metallic materials, so it would not affect the NFC antenna performance. Test results show a read range of 10 mm with the metal clip assembled on the sensor.

In an embodiment, a size of an antenna for the UV sensor may be adjusted from 9 mm to 9.4 mm (for example). Such an antenna has significant improvement on the Q factor from 20 to 41, and increased read range from 1 mm to 10 mm (when tested with an iPhone).

Figure 25:
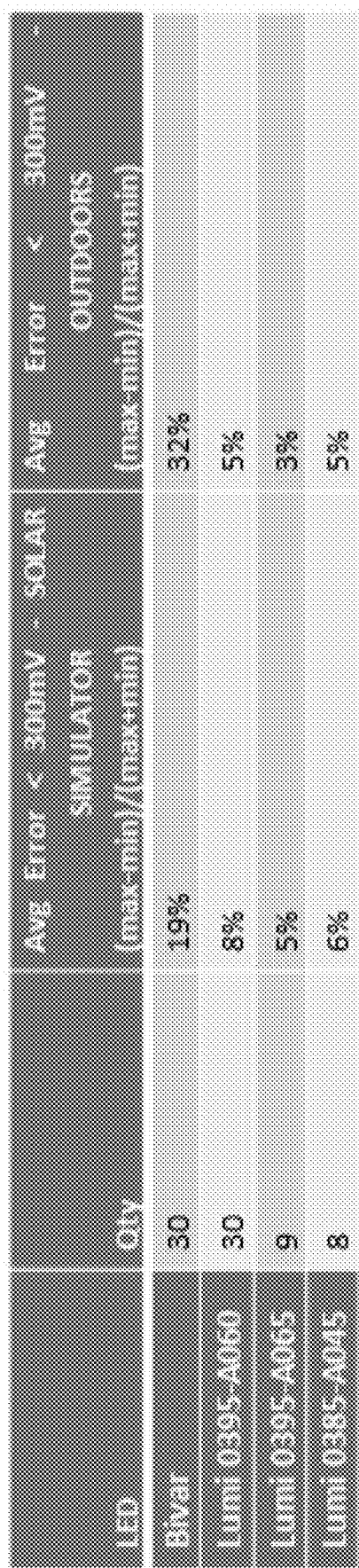
FIGS. 25-26 show test results of UV sensors with various types of LEDs.

The present inventors further discovered that there is a large sample to sample variation when the sensors are placed outdoor in the same condition, primarily due to the viewing angle and manufacture quality of the UV LED. When a Bivar-395 LED was used, the sample to sample variation is about 32% when testing outdoor. Another UV LED Part (Lumi 0395-A065) was tested to improve the sample to sample variation to ~5%. The test results are included in the table shown on FIG. 25.

Figure 26:

The LED used in one embodiment (Bivar UV LED) has a viewing angle of ±30 degrees, which will limit the sensor responses when the device is placed on different parts of body (wrist, shoulder, or sleeve) with tilted angle. Another UV Led (LHUV-0395-A060) was selected with wider viewing angle for ±130 degrees. The test results are shown in the table on FIG. 26, with controlled source light from Solar Simulator.

The inventors further discovered that there is a significant bounce back voltage in the super capacitor after the sensor is being reset with the transistor. The bounce back voltage can be characterized and incorporated into the UVA dosage calculation based on the following table.

| V (voltage_previous_initial), mV | bounce back voltage (mV) |
|---|---|
| V >= 200 | 15 |
| 100 <= V < 200 | 15 |
| 11 <= V < 100 | 5 |
| V < 11 | 0 |

Figure 27:
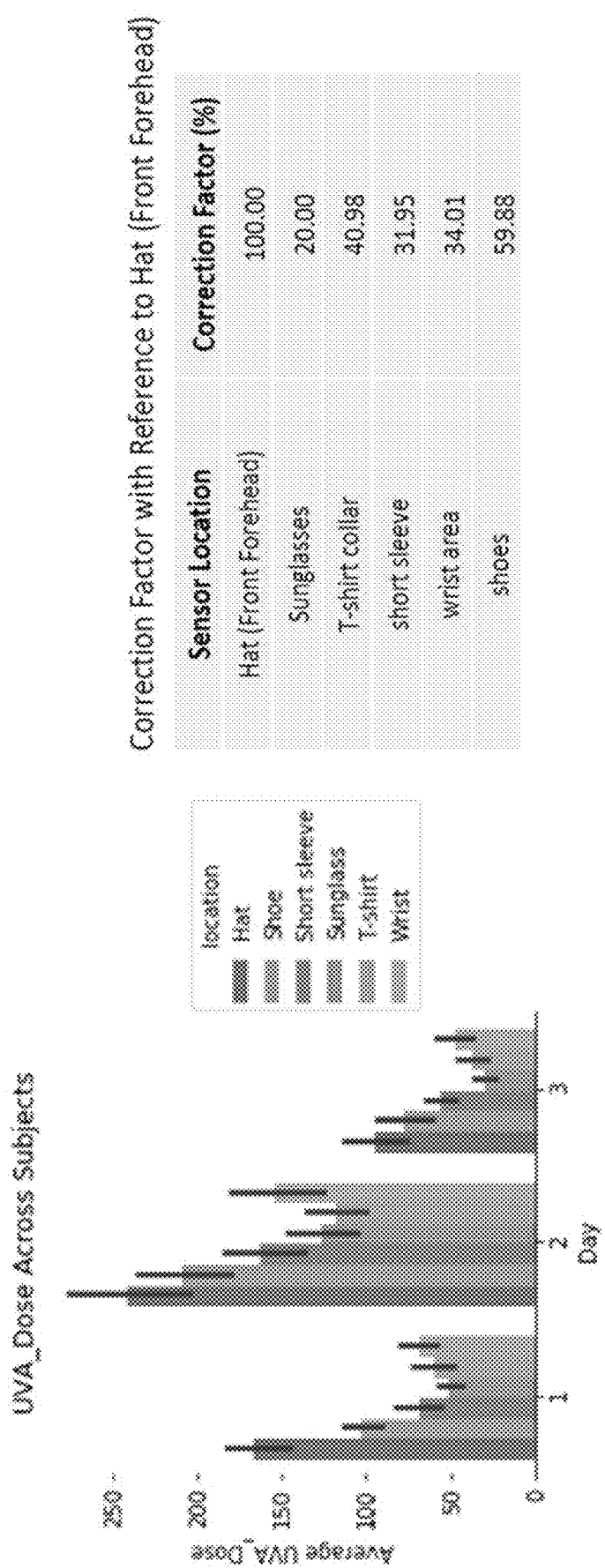
FIG. 27 shows a UV dosage and correction factor based on sensor placement on various parts of the body.

The inventors further developed a study protocol to understand the correction factor if the sensor is placed on different body locations. The algorithm will compute the maximum UV dosage on the body (forehead, shoulder, top of head) based on the sensor locations as shown in FIG. 27.

Figure 28A:
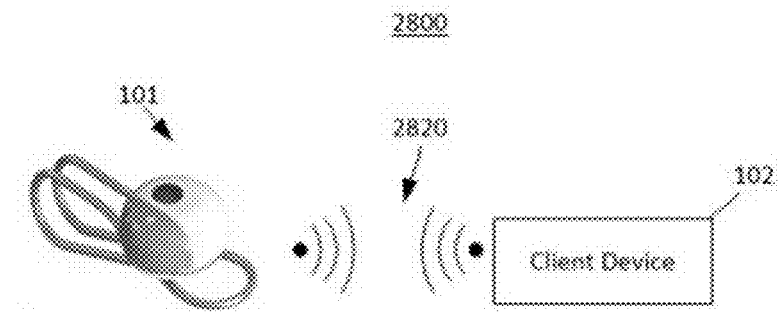
FIG. 28A shows a system that includes the UV sensor and a client device according to an embodiment.

FIG. 28A shows a system 2800 that includes the UV sensor 101 and a client device 102. In an embodiment, the UV sensor 101 is in communication with the client device 102 with a wireless signal 2820. In an embodiment, the client device 102 is configured to operate a software application or set of software modules to receive and send communications from and to the UV sensor 101. In an example, the software application tracks the UV sensor's UV measurements in real time.

Figure 28B:
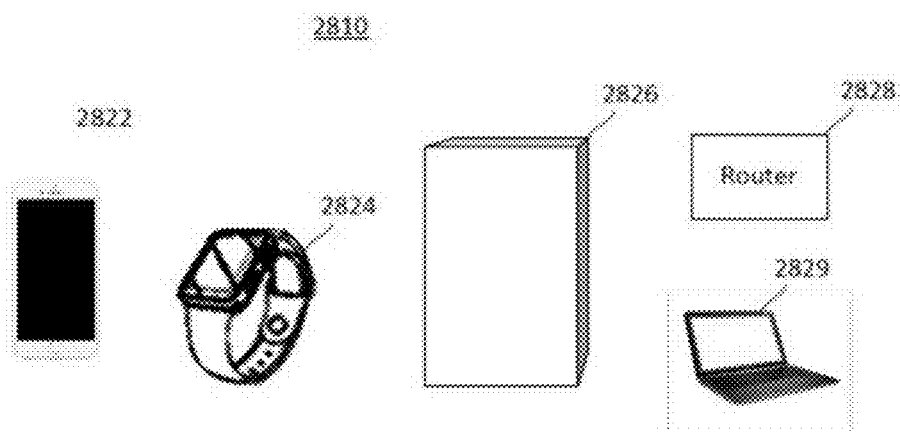
FIG. 28B shows different examples of the client device according to an embodiment.

FIG. 28B shows different examples of the client devices 102 including, a mobile device 2822, a wearable electronic 2824, a television or magic mirror 2826, a network router 2828, and a personal computer 2829.

The wireless signal 2820 can be any appropriate signal such as an electromagnetic signal including WIFI, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 28C:
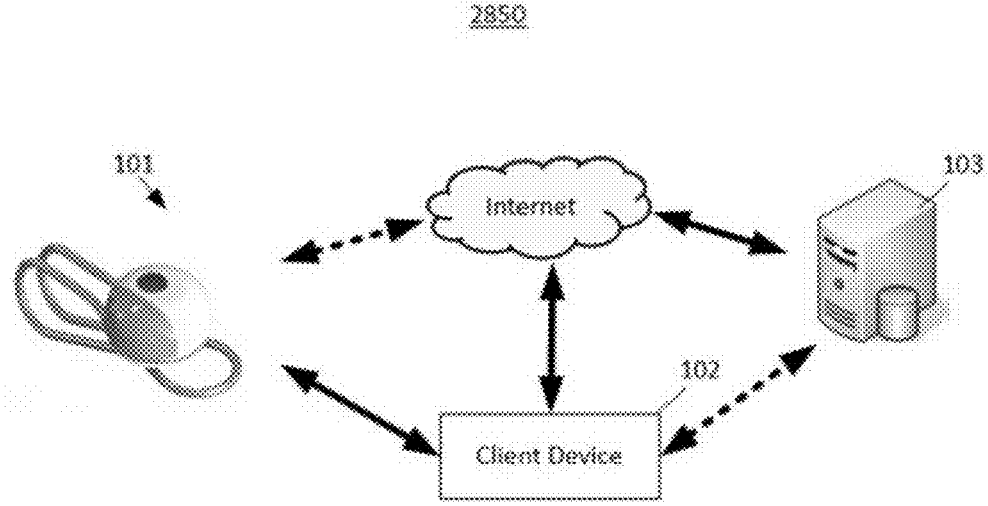
FIG. 28C is a diagram representing an example of a system to promote optimum performance of a UV sensor, according to an embodiment.

FIG. 28C is a diagram representing an example of a system 550 (similar to FIG. 1) to promote optimum performance of a UV sensor, according to one example. The system 2850 includes at least the UV sensor and the client device. Optionally, the system 2850 may further include one or more servers 103 which are implemented as part of a cloud-computing environment and in communication with the system 2850 through the Internet. The one or more external servers 103 can store user data, products such as skincare products, skincare accessories, protocols and routines, tutorials, as well as other $3^{rd}$ party services according to an example.

The user interface or the client device can display tutorials on how to use skincare products or accessories. The user interface can create and download protocols for a regimen or routine. The user interface can coach, track usage and compare the tracked usage to the protocol, the regimen, and the routine. The user interface can calculate a score based on the tracked usage. The user interface can store the scores and the tracked usage of any appliances in the memory of the client device, or it can be uploaded to the cloud server 103. The user interface can be used to make a purchase of any products related to skincare or UV protection. For instance, the client device can output recommendations on particular skincare products or compositions to be used, and which step in the process they are to be used, based on the desired results inputted by the user.

As an initial step, the client device collects information regarding a user's desired results. The client device may store search results locally or may connect to an external system or server to access the database or search results.

After the user finds a desired skincare results, the user may access tutorials for achieving the results. The tutorials may be in text form, still image form, video form, or audio-only form.

The client device can also have a camera function that can be used to provide inputs to the customer profile. For instance, the camera can take images of the user's skin to determine if a desired look is possible, or to make further recommendations to the user based on the characteristics or color of the skin.

The client device is configured to upload data regarding the user to an external system or server (such as a cloud-based system). Such data may include the user profile, amount of use of skincare products or accessories, or performance results when using the skincare products or accessories. The client device can also provide an option to keep the user data anonymous.

Furthermore, the circuitry of the client device may be configured to actuate a discovery protocol that allows the client device and the UV sensor to identify each other and to negotiate one or more pre-shared keys, which further allows the UV sensor and the client device to exchanged encrypted and anonymized information.

Figure 29:
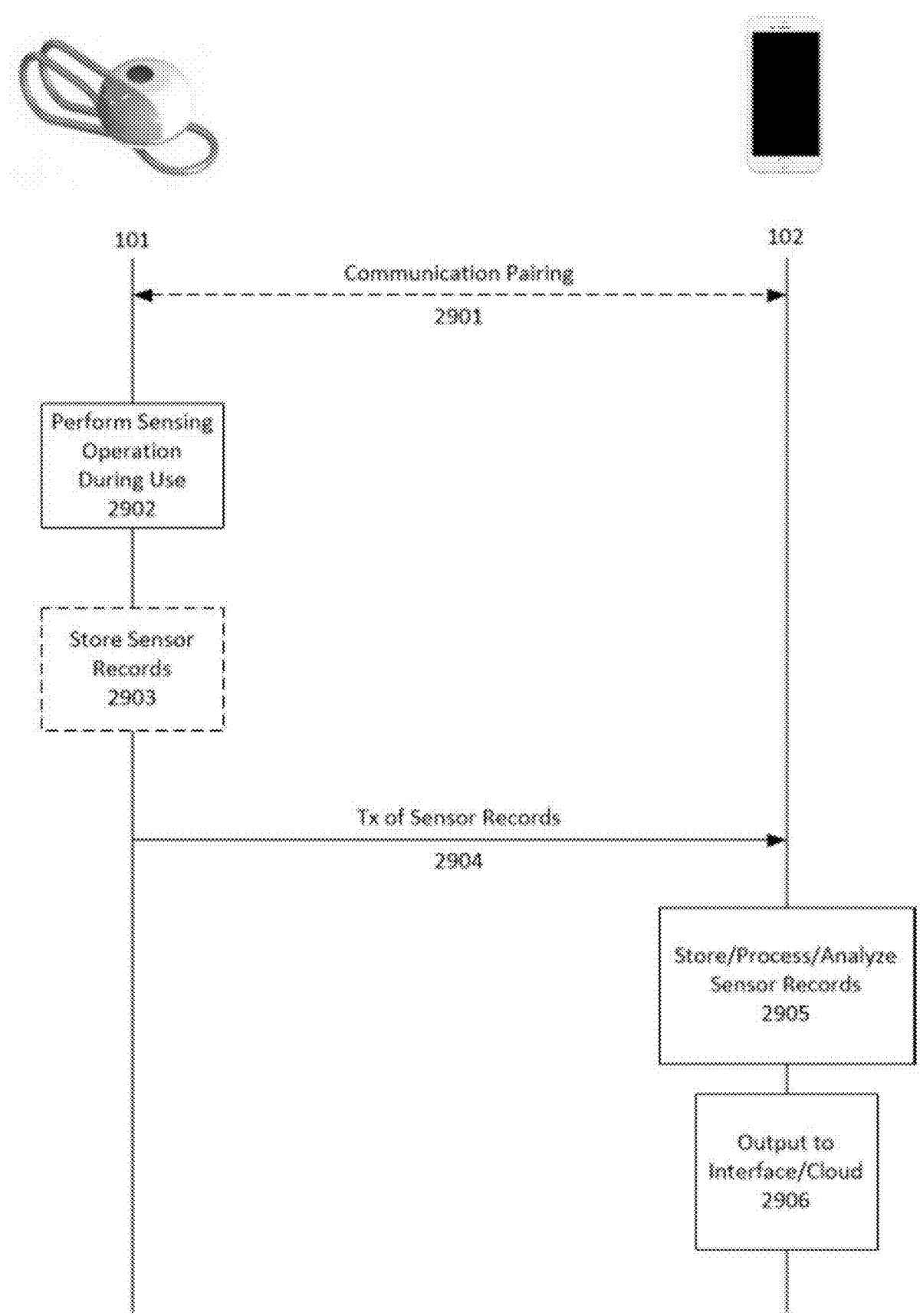
FIG. 29 shows a general process performed among the UV sensor and the client device according to an embodiment.

FIG. 29 shows a general processes performed among the UV sensor 10 and the client device 102. Communication pairing 2901 is performed between the two devices when the two devices are within an acceptable wireless communication range of each other. Such pairing will depend on the type of communication protocol being used and such protocols are well understood in the art. The UV sensor perform any of a number of sensing operations for taking UV measurements as was described above. The sensor records obtained by the sensing operations may be optionally stored in a local memory (step 2903) and/or immediately communicated to the client device 102 (step 2904).

As shown in FIG. 29, the client device stores the sensed data received from the UV sensor, and performs processing and analyzing of the sensed data (step 2905), as was discussed above. Then, the client device 102 then may output the results on the display of the client device as is described above, and/or the client device may output such results or other data to a cloud server, such as cloud server 103 shown in FIG. 1.

Figure 30:
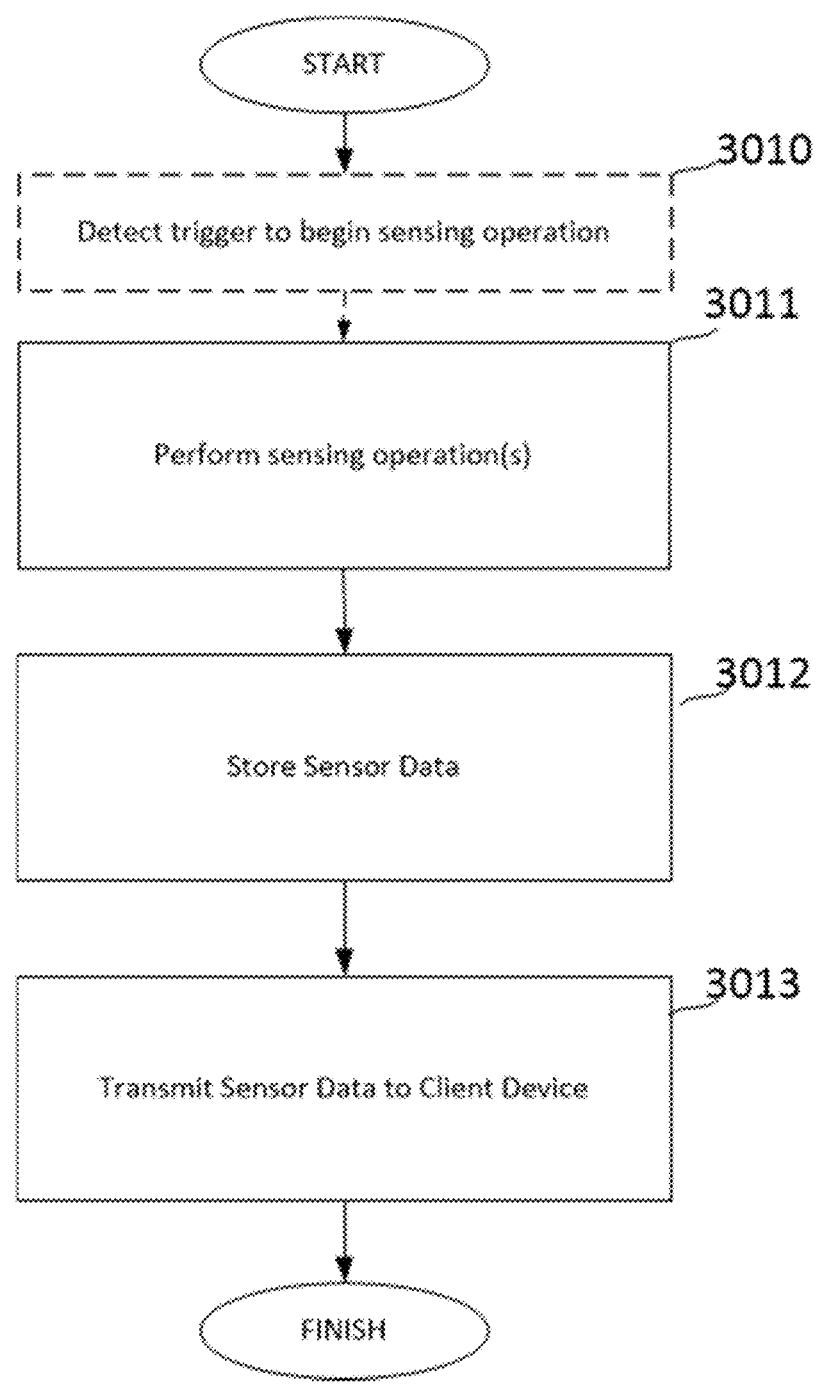
FIG. 30 shows an algorithm that may be performed by the UV sensor according to an embodiment.

FIG. 30 shows an algorithm that may be performed by the UV sensor according to an embodiment. In step 3010, the UV sensor detects a trigger to begin sensing operation. This trigger may be automatic activation based on any exposure to the sun. The trigger may also be received from the client device itself. For instance, if communication pairing has been established between the UV sensor and the client device, the client device may transmit a signal to the UV sensor to begin the sensing operation.

The sensing operation(s) is/are performed at step 3011. The types of sensing operations performed by the UV sensor are described in detail above. In step 3012, the sensor data obtained from the sensing operations are optionally stored in the memory of the UV sensor as they are obtained. In step 3012, the sensor data is transmitted to the client device. Such transmission may be made when the data is accumulated after a total amount of time, it may occur periodically, it may occur based on user input at the client device, or it may occur based on a request signal received from the client device.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive.

It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A device configured to measure ultra-violet (UV) radiation exposure, comprising:
   an electronic element configured to detect UV radiation exposure;
   circuitry configured to transmit detected UV radiation exposure to an external device;
   an antenna that is at least 9.4 mm; and
   a clip that is made of a metallic material that is in a form of a closed loop that is folded over on itself,
   wherein a read range between the device and a terminal device configured to receive an output of the measured UV irradiation from the measurement device is at least 10 mm.

2. The device according to claim 1, wherein the electronic element is a UV sensitive LED.

3. The device according to claim 2, wherein the circuitry includes a near field communication device.

4. The device according to claim 1, further comprising a flexible material which encapsulates the electronic element and the circuitry.

5. The device according to claim 1, wherein the device is configured to attach to a user's fingernail.

6. The device according to claim 1, wherein the circuitry is configured to transmit the detected UV radiation exposure to the external device at regular intervals.

7. The device according to claim 1, wherein the circuitry is configured to transmit the detected UV radiation exposure to the external device at upon request from the external device.

8. A system for determining personal ultra-violet (UV) radiation measurements, comprising:
   a measurement device configured to measure UV irradiation at one of a plurality of predetermined locations on a user; and
   a terminal device configured to receive an output of the measured UV irradiation from the measurement device and to display a specific user's personal UV exposure risk level based on at least the measured sun irradiation,
   wherein the terminal device is configured to apply a correction factor, from a plurality of predetermined correction factors corresponding respectively to the plurality of predetermined locations on the user, to the measured UV irradiation based on the location of the measurement device on the user.

9. The system according to claim 8, wherein the terminal device is configured to receive the measured UV irradiation from the measurement device at regular intervals over a predetermined time period, and display the specific user's personal UV exposure risk level based the measured sun irradiation taken over the entire predetermined time period.

10. The system according to claim 9, wherein the terminal device is configured to correlate information related to specific user activities over the predetermined time period to the measured sun irradiation received from the measurement device.

11. The system according to claim 1, wherein the terminal device is configured to correlate information of a skin type of the user and the measured UV irradiation received from the measurement device.

12. The system according to claim 1, wherein the terminal device is configured to output a recommended method of protection or action based on the measured UV irradiation received from the measurement device.

13. A method, implemented by a system for determining personal ultra-violet (UV) radiation measurements, comprising:
   measuring, with a measurement device, UV irradiation at one of a plurality of predetermined locations on a user; and
   receiving, by a terminal device, an output of the measured UV irradiation from the measurement device and displaying a specific user's personal UV exposure risk level based on at least the measured sun irradiation,
   wherein the terminal device is configured to apply a correction factor, from a plurality of predetermined correction factors corresponding respectively to the plurality of predetermined locations on the user, to the measured UV irradiation based on the location of the measurement device on the user.

14. The system according to claim 8, wherein UVA and UVB exposure is calculated based on the measured UV irradiation, and the UVB exposure calculated using a pre-computed lookup table that provides a conversion factor as a function of an amount of ozone in the atmosphere and a solar zenith angle (SZA), the SZA being determined based on a detected global positioning system (GPS) location and time.

* * * * *